US011058889B1

(12) United States Patent
Suntych

(10) Patent No.: US 11,058,889 B1
(45) Date of Patent: Jul. 13, 2021

(54) METHOD OF USING PHOTON MODULATION FOR REGULATION OF HORMONES IN MAMMALS

(71) Applicant: Xiant Technologies, Inc., Greeley, CO (US)

(72) Inventor: Jon Daren Suntych, Greeley, CO (US)

(73) Assignee: Xiant Technologies, Inc., Greeley, CO (US)

(*) Notice: Subject to any disclaimer, the term of this patent is extended or adjusted under 35 U.S.C. 154(b) by 267 days.

(21) Appl. No.: 15/944,400

(22) Filed: Apr. 3, 2018

Related U.S. Application Data

(60) Provisional application No. 62/480,685, filed on Apr. 3, 2017.

(51) Int. Cl.
| | | |
|---|---|---|
| *A61N 5/06* | (2006.01) | |
| *A01K 21/00* | (2006.01) | |
| *A01K 67/02* | (2006.01) | |

(52) U.S. Cl.
CPC ............ *A61N 5/0616* (2013.01); *A01K 21/00* (2013.01); *A01K 67/02* (2013.01); *A61N 5/062* (2013.01);
(Continued)

(58) Field of Classification Search
CPC .................. A61N 5/0616; A61N 5/062; A61N 2005/063; A61N 2005/0627;
(Continued)

(56) References Cited

U.S. PATENT DOCUMENTS

| 2,300,727 A | 11/1942 | Durling |
|---|---|---|
| 2,986,842 A | 6/1961 | Toulmin, Jr. |
| (Continued) | | |

FOREIGN PATENT DOCUMENTS

| CN | 203840585 U | 9/2014 |
|---|---|---|
| EP | 1374665 | 1/2004 |
| (Continued) | | |

OTHER PUBLICATIONS

Hendricks, Sterling B.; How Light Interacts With Living Matter; Scientific American, Inc.; 1968; pp. 175-186.
(Continued)

*Primary Examiner* — Mark Bockelman
(74) *Attorney, Agent, or Firm* — Weatherly IP Solutions, LLC; James M. Weatherly

(57) ABSTRACT

Embodiments of the present disclosure provide systems, apparatuses and methods for regulation hormone production in mammals. Examples include but are not limited to by creating electro-magnetic wave emission pulse trains (photons) of individual color spectrums in sufficient intensity to drive hormone production in a mammal, using a characteristic frequency or pattern to minimize the required input power necessary to regulate hormone production, while also allowing for the monitoring of the power consumption and other variables of the system. By controlling the duty cycle, intensity, wavelength band and frequency of photon signals to a mammal, production of specific hormones can be regulated through the cycling between blue, green, yellow, near-red, far-red, infrared and ultra violet photon modulation.

34 Claims, 23 Drawing Sheets

(52) U.S. Cl.
CPC ...... *A61N 2005/063* (2013.01); *A61N 2005/0627* (2013.01); *A61N 2005/0629* (2013.01); *A61N 2005/0658* (2013.01)

(58) Field of Classification Search
CPC .... A61N 2005/0629; A61N 2005/0658; A01K 21/00; A01K 67/02
See application file for complete search history.

(56) References Cited

U.S. PATENT DOCUMENTS

| | | | |
|---|---|---|---|
| 3,089,280 A | 5/1963 | Klaas | |
| 3,352,058 A | 11/1967 | Brant | |
| 3,703,051 A | 11/1972 | Weinberger | |
| 3,876,907 A | 4/1975 | Widmayer | |
| 3,930,335 A | 1/1976 | Widmayer | |
| 3,931,695 A | 1/1976 | Widmayer | |
| 4,396,872 A | 8/1983 | Nutter | |
| 4,749,916 A | 6/1988 | Yamazaki et al. | |
| 5,012,609 A | 5/1991 | Ignatius et al. | |
| 5,173,737 A | 12/1992 | Mitchell | |
| 5,381,075 A | 1/1995 | Jordan | |
| 5,454,187 A | 10/1995 | Wasserman | |
| 5,675,931 A | 10/1997 | Wasserman | |
| 5,818,734 A | 10/1998 | Albright | |
| 6,396,938 B1 | 5/2002 | Tao | |
| 6,615,538 B2 | 9/2003 | Hittin | |
| 6,860,225 B2 | 3/2005 | Hebrank | |
| 6,940,424 B2 | 9/2005 | Philiben | |
| 7,160,717 B2 | 1/2007 | Everett | |
| 7,600,343 B2 | 10/2009 | Schultheiss et al. | |
| 7,993,381 B2 * | 8/2011 | Mac ............... | A61N 5/0619 607/88 |
| 8,074,397 B2 | 12/2011 | Yoneda et al. | |
| 8,181,387 B2 | 5/2012 | Loebl et al. | |
| 8,302,346 B2 | 11/2012 | Hunt et al. | |
| 8,384,047 B2 | 2/2013 | Shur et al. | |
| 8,596,804 B2 | 12/2013 | Grajcar | |
| 8,847,514 B1 | 9/2014 | Reynoso et al. | |
| 8,858,005 B2 | 10/2014 | Grajcar | |
| 8,876,313 B2 | 11/2014 | Grajcar | |
| 9,016,240 B2 | 4/2015 | Delabbio | |
| 9,185,888 B2 | 11/2015 | Grajcar | |
| 9,433,194 B2 | 9/2016 | Grajcar et al. | |
| 9,482,397 B2 | 11/2016 | Grajcar | |
| 9,526,215 B2 | 12/2016 | Suntych | |
| 9,560,837 B1 | 2/2017 | Suntych | |
| 9,675,054 B2 | 6/2017 | Grajcar et al. | |
| 9,700,019 B2 | 7/2017 | Grajcar | |
| 9,709,228 B2 | 7/2017 | Grajcar | |
| 9,756,837 B2 | 9/2017 | Grajcar | |
| 9,844,209 B1 | 12/2017 | Suntych | |
| 9,844,210 B2 | 12/2017 | Grajcar et al. | |
| 9,907,296 B2 | 3/2018 | Suntych | |
| 10,028,448 B2 | 7/2018 | Grajcar et al. | |
| 10,182,557 B2 | 1/2019 | Suntych | |
| 10,609,909 B2 | 4/2020 | Suntych | |
| 10,638,669 B2 | 5/2020 | Suntych | |
| 2003/0009933 A1 | 1/2003 | Yoneda et al. | |
| 2003/0172878 A1 | 9/2003 | El Halawani et al. | |
| 2004/0109302 A1 | 6/2004 | Yoneda et al. | |
| 2005/0076563 A1 | 4/2005 | Faris | |
| 2005/0152143 A1 | 7/2005 | Lee et al. | |
| 2005/0152146 A1 | 7/2005 | Owen et al. | |
| 2005/0248962 A1 * | 11/2005 | Searfoss, III ......... | A61M 21/02 362/642 |
| 2007/0151149 A1 | 7/2007 | Karpinski | |
| 2009/0007486 A1 | 1/2009 | Corradi | |
| 2009/0047722 A1 | 2/2009 | Wilkerson et al. | |
| 2009/0280223 A1 | 11/2009 | Scott | |
| 2010/0115830 A1 | 5/2010 | Dube | |
| 2010/0121131 A1 | 5/2010 | Mathes | |
| 2010/0217358 A1 | 8/2010 | Herbert | |
| 2010/0236497 A1 | 9/2010 | Philiben | |
| 2010/0244724 A1 | 9/2010 | Jacobs et al. | |
| 2011/0109236 A1 | 5/2011 | Zhurin | |
| 2011/0115385 A1 | 5/2011 | Waumans et al. | |
| 2011/0159562 A1 | 6/2011 | Deisseroth et al. | |
| 2011/0209404 A1 | 9/2011 | Scott | |
| 2012/0042419 A1 | 2/2012 | Wilson et al. | |
| 2012/0067296 A1 | 3/2012 | Hornung | |
| 2012/0107792 A1 | 5/2012 | Babbitt et al. | |
| 2012/0107921 A1 | 5/2012 | Willson et al. | |
| 2012/0270304 A1 | 10/2012 | Johnson et al. | |
| 2012/0293472 A1 | 11/2012 | Wong et al. | |
| 2013/0008085 A1 | 1/2013 | Aikala et al. | |
| 2013/0023044 A1 | 1/2013 | Gleason | |
| 2013/0042523 A1 | 2/2013 | Lee et al. | |
| 2013/0042527 A1 | 2/2013 | Aikala et al. | |
| 2013/0044474 A1 | 2/2013 | Aikala et al. | |
| 2013/0047503 A1 | 2/2013 | Aikala et al. | |
| 2013/0076239 A1 | 3/2013 | Chung et al. | |
| 2013/0139437 A1 | 6/2013 | Maxik | |
| 2014/0158050 A1 | 6/2014 | Grajcar | |
| 2014/0250778 A1 | 9/2014 | Suntych | |
| 2015/0150195 A1 | 6/2015 | Grajcar | |
| 2015/0237890 A1 | 8/2015 | Grajcar | |
| 2015/0273235 A1 | 10/2015 | Grajcar | |
| 2016/0014974 A1 | 1/2016 | Grajcar et al. | |
| 2016/0120155 A1 | 5/2016 | Grajcar | |
| 2016/0165698 A1 | 6/2016 | Grajcar | |
| 2016/0165859 A1 | 6/2016 | Grajcar | |
| 2017/0000163 A1 | 1/2017 | Grajcar | |
| 2017/0071166 A1 | 3/2017 | Grajcar et al. | |
| 2017/0071167 A1 | 3/2017 | Grajcar et al. | |
| 2017/0071168 A1 | 3/2017 | Grajcar et al. | |
| 2017/0074464 A1 | 3/2017 | Grajcar et al. | |
| 2017/0105391 A1 | 4/2017 | Grajcar | |
| 2017/0135325 A1 | 5/2017 | Grajcar et al. | |
| 2017/0259079 A1 | 9/2017 | Grajcar et al. | |
| 2017/0290124 A1 | 10/2017 | Grajcar | |
| 2017/0347532 A1 | 12/2017 | Suntych | |
| 2018/0125040 A1 | 5/2018 | Grajcar et al. | |

FOREIGN PATENT DOCUMENTS

| | | |
|---|---|---|
| EP | 2044835 A1 | 4/2009 |
| JP | 4-75779 A | 3/1992 |
| JP | 9-275779 A | 10/1997 |
| JP | 10-178899 A | 7/1998 |
| JP | 2014064479 | 4/2014 |
| JP | 2015-192654 | 11/2015 |
| WO | 2001/62070 A1 | 8/2001 |
| WO | 2009046548 A3 | 4/2009 |
| WO | 2011086358 A2 | 7/2011 |
| WO | 2011/115123 A1 | 9/2011 |
| WO | 2013/113096 W1 | 8/2013 |
| WO | 2014/138262 A1 | 9/2014 |
| WO | 2015/106380 A1 | 7/2015 |
| WO | 2016/033350 A1 | 3/2016 |

OTHER PUBLICATIONS

PCT/US2014/20809—International Search Report and Written Opinion, dated Jun. 20, 2014.
Response to USPTO non-final office action, U.S. Appl. No. 14/197,949 (Publication 20140250778), dated May 13, 2016.
Non-Final Office Action, U.S. Appl. No. 14/197,949, dated Feb. 17, 2016.
PCT/US2015/047239—International Search Report and Written Opinion, dated Aug. 27, 2015.
PCT/US2016/054197—International Search Report and Written Opinion, dated Feb. 9, 2017.
Non-Final Office Action, U.S. Appl. No. 15/385,517, dated Jun. 26, 2017.
Response to USPTO non-final office action, U.S. Appl. No. 15/385,517, dated Sep. 18, 2017.
EPO Application No. 14761009, European Search Report, dated Sep. 12, 2016.
JP Application No. 2015-561614, English translation of Final Office Action dated Oct. 31, 2017.

(56) References Cited

OTHER PUBLICATIONS

CN Application No. 201480011700.9, English translation of Office Action dated Sep. 5, 2017.
Response to USPTO final office action, U.S. Appl. No. 15/385,517, dated Apr. 20, 2018.
CN Application No. 201680073509.6, English translation of Office Action dated Dec. 4, 2018.
CN Application No. 201680073509.6, English translation of Office Action dated May 24, 2019.
NZ Application No. 742370, Office Action dated May 22, 2019.
Response to office action as filed, CN Application No. 201680073509.6, dated Mar. 2019.
NZ Application No. 742370, First Office Action dated Oct. 30, 2018.
Response as filed NZ Application No. 742370, First Office Action dated Apr. 24, 2019.
EP Application No. 16781253.6, First office action dated May 29, 2019.
Response as filed EP Application No. 16781253.6, dated Oct. 7, 2019.
Response as filed in U.S. Appl. No. 15/385,517, dated Feb. 26, 2020.
JP Application No. 2015-561614, English translation of Office Action dated May 23, 2017.
Japan Application: 2018-525590, Notice of Reasons for Rejection; dated Nov. 5, 2019.
Japan Application: 2018-525590, Response as filed Feb. 4, 2020.

\* cited by examiner

Melatonin Elisa Kit Standard Curve showing the concentrations ranging from 0.04 ng/mL to 50 ng/mL. The reading of blank is not show on the plot because of the log-scale of X axis.

METHOD OF USING PHOTON MODULATION FOR REGULATION OF HORMONES IN MAMMALS

CROSS REFERENCE TO RELATED APPLICATION

The present application claims priority to U.S. Application No. 62/480,685, as filed on Apr. 3, 2017, entitled "PHOTON MODULATION MANAGEMENT SYSTEM FOR STIMULATION OF A DESIRED RESPONSE IN MAMMALS AND FISH", the entire contents of which are incorporated herein by reference for all purposes.

SUMMARY

The following embodiments and aspects thereof are described and illustrated in conjunction with systems, tools and methods, which are meant to be exemplary and illustrative, not limiting in scope.

An embodiment of the present invention comprises a method of regulation of hormones in mammals, the method comprising: providing a system for pulsing photon signals toward a mammal comprising: at least one photon emitter; at least one photon emission modulation controller in communication with the photon emitter; where the at least one photon emitter is configured to produce a photon signal directed toward the mammal, where the photon signal comprises two or more independent components, where the two or more independent components comprise: a first independent component of a repetitive first modulated photon pulse group, where the first modulated photon pulse group has one or more first photon pulse ON durations with one or more first intensities, has one or more first photon pulse OFF durations, and a first wavelength color; where the one or more durations of the first photon pulse ON is between 0.01 microseconds and 5000 milliseconds and where the one or more durations of the first photon OFF is between is between 0.1 microseconds and 24 hours; and a second independent component of a repetitive second modulated photon pulse group, where the second modulated photon pulse group has one or more second photon pulse ON durations with one or more second intensities, has one or more second photon pulse OFF durations, and a second wavelength color; where the one or more durations of the second photon pulse ON is between 0.01 microseconds and 5000 milliseconds and where the one or more durations of the second photon OFF is between is between 0.1 microseconds and 24 hours; where the first independent component and the second independent component are produced within the signal simultaneously; where the second modulated photon pulse group is different from the first modulated photon pulse group; and emitting the signal toward the mammal; where the combined effect of the signal is regulation of hormone levels in the mammal when compared to the established baseline hormone level of the mammal and/or, the modification of behavior, reproduction cycling, hair growth, calming or metabolism rates.

An embodiment of the present invention further comprises a system for regulating hormone production in a mammal, comprising: at least one photon emitter; at least one photon emission modulation controller in communication with the at least one photon emitter; where the at least one photon emitter is configured to produce a photon signal to the mammal, where the where the photon signal comprises two or more independent components, where the two or more independent components comprise: a first independent component of a repetitive first modulated photon pulse group, where the first modulated photon pulse group has one or more first photon pulse ON durations with one or more first intensities, has one or more first photon pulse OFF durations, and a first wavelength color; where the one or more durations of the first photon pulse ON is between 0.01 microseconds and 5000 milliseconds and where the one or more durations of the first photon OFF is between is between 0.1 microseconds and 24 hours; and a second independent component of a repetitive second modulated photon pulse group, where the second modulated photon pulse group has one or more second photon pulse ON durations with one or more second intensities, has one or more second photon pulse OFF durations, and a second wavelength color; where the one or more durations of the second photon pulse ON is between 0.01 microseconds and 5000 milliseconds and where the one or more durations of the second photon OFF is between is between 0.1 microseconds and 24 hours; where the first independent component and the second independent component are produced within the signal simultaneously; where the second modulated photon pulse group is different from the first modulated photon pulse group; and where the signal toward the mammal has the combined effect of the first photon pulse group and the second photon pulse group regulates hormone production in the mammal and/or, the modification of behavior, reproduction cycling, hair growth, calming or metabolism rates.

BRIEF DESCRIPTION OF THE FIGURES

The accompanying drawings, which are incorporated herein and form a part of the specification, illustrate some, but not the only or exclusive, example embodiments and/or features. It is intended that the embodiments and figures disclosed herein are to be considered illustrative rather than limiting.

FIG. 8b is a photo showing the backside of the multiple colored die within a single LED of FIG. 8a.

FIG. 8c is a photo showing the high-speed switching circuitry for flashing of the multiple colored die within a single LED of FIG. 8a.

DETAILED DESCRIPTION

Figure 1:
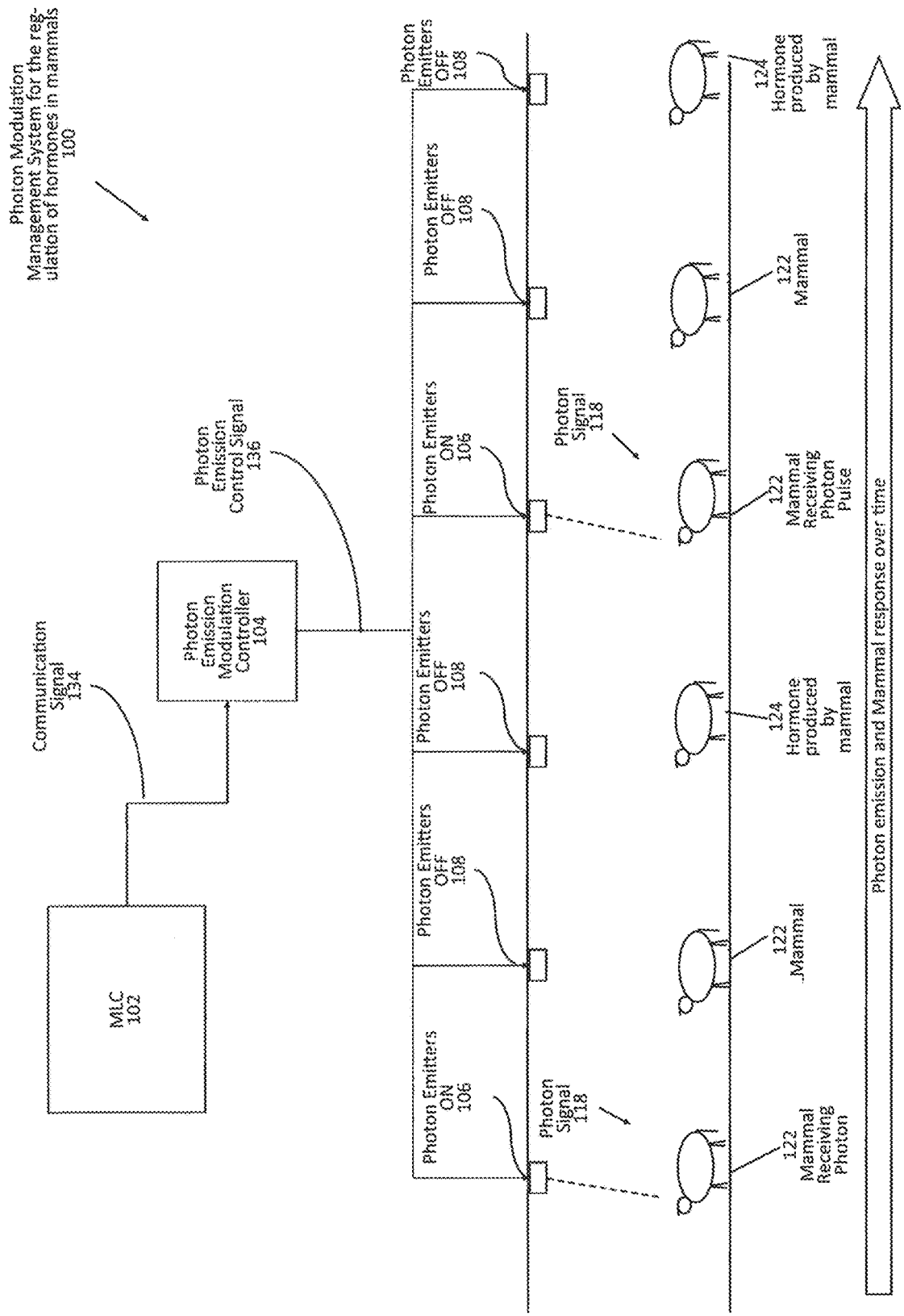
FIG. 1 is a diagram showing an example of a photon modulation growth system for regulation of hormones in a mammal.

Embodiments of the present disclosure provide systems, apparatuses and methods for regulation of hormone production in mammals, where the hormones to be regulated may include, but are not limited to, hypothalamic hormones, such as corticotropin-releasing hormone, prolactin-releasing factors (serotonin, acetylcholine, opiates, & estrogens), somatostatin, prolactin-inhibiting factors (dopamine), pituitary hormones such as adrenocorticotropic hormone (ACTH), melanocyte-stimulating hormone, endorphins, growth hormone, luteinizing hormone (LH) and follicle-stimulating hormone (FSH), thyroid-stimulating hormone (TSH), prolactin, epinephrine, melatonin, leukotrienes, follicle-stimulating hormone, growth hormones, insulin, insulin-like growth factor, oxytocin, parathyroid hormone, thyrotropin-releasing hormone, testosterone, estradiol and progesterone. The systems and methods described herein include, but are not limited to, creating electro-magnetic wave emission pulse trains (photons) of individual color spectrums in sufficient intensity to drive hormone production in a mammal, as well as using a characteristic frequency or pattern to minimize the required input power necessary to regulate hormone production, while also allowing for the monitoring of the power consumption and other variables of the system. As will be discussed in further detail, by controlling the duty cycle, intensity, wavelength band and frequency of photon signals to a mammal, production of specific hormones can be regulated through the cycling between blue, green, yellow, near-red, far-red, infrared and ultra violet photon modulation.

Specifically, by combining multiple repetitive wavelengths of photons pulses into photon signals at specific combination of pulse rates, hormone production by mammals can be regulated and optimized, including allowing for an increase in the production of specific hormones from 0.1%, 1.0%, 5%, 7.5, 10%, 12.2%, 20%, 33.3%, 50%, 81.7%, 100%, 143.9%, 150%, 181.4%, 200%, 250%, 444.2%, 500% and 1000% or more and all integers in between, over the baseline hormone level of a mammal, or a decrease in the production of specific hormones from 0.1%, 1.2%, 7.7%, 10%, 15.6, 20%, 47.2%, 50%, 74.5%, 100%, 150%, 200%, 250%, 500% and 1000% or less and all integers in between, under the baseline hormone level of a mammal as in the mammal, along with regulation or control of a mammal's mood by reducing stress or calming the mammal.

The embodiments of the present disclosure provided herein regulate the production of specific hormones. Each light "recipe" or option (a photon signal having one or more repetitive modulated photon pulse groups with one or more first photon pulse ON durations with one or more first intensities, one or more first photon pulse OFF durations, and a first wavelength color) can be optimized for each hormone to be regulated to each species of mammal.

An additional example embodiment to the methods, systems and apparatuses described herein may include less heat creation: LED lighting intrinsically creates less heat than conventional lights. When LED lights are used in a dosing application, they are ON less than they are OFF. This creates an environment with nominal heat production from the LED lights. This is not only beneficial in terms of not having to use energy to evacuate the heat from the system but is beneficial to the mammal because lighting may also be used to reduce animal stress or calm the animal.

Regulation of Hormones

The hypothalamus functions as the coordinating center of the endocrine system. Inputs from the somatic and autonomic nervous system, peripheral endocrine feedback, and environmental cues such as light and temperature are processed in the hypothalamus. The hypothalamus then affects the function of multiple endocrinologic systems via hypothalamic-pineal interaction (via the suprachiasmatic nucleus) and the hypothalamic-pituitary axis. The hypothalamus is responsible for control of the circadian rhythm, temperature regulation, and metabolism. Hypothalamic hormones also affect pituitary hormone production. Pituitary hormones control adrenal, thyroid, and gonadal function in addition to water balance, growth, modification of behavior, reproduction cycling, hair growth, calming or metabolism rates. and milk production.

The hypothalamus is located in the middle of the head. It is posterior to the eyes and sits just below the third ventricle and above the optic chiasm and pituitary gland. Afferent inputs to the hypothalamus originate from the brainstem, thalamus, basal ganglia, cerebral cortex, olfactory areas, and the optic nerve. Efferent pathways go to the brainstem reticular centers, autonomic nervous system, thalamus, pineal gland, median eminence, and the hypothalamo-neurohypophysial tract which connects the paraventricular and supraoptic nuclei to nerve terminal in the posterior pituitary.

In mammals, the eye functions as the primary source of photoreceptors and subsequently light input. This primarily occurs through the rods/cones in the retina that utilize opsin-based proteins (chromophores). Rhodopsin in the best known of these photoreceptors in mammals. A novel photopigment, melanopsin, has also been identified in retinal ganglion cells named ipRGCs (intrinsically photosensitive retinal ganglion cells), but do not have classic photoreceptive tasks. Opsins are known to be widely expressed in other mammalian tissues but the utility and function of these is not as well documented. OPN3 is one example of an extraocular opsin. OPN3 is expressed in the brain, testis, liver, placenta, heart, lung, muscle, kidney, pancreas, scrotum and skin.

Visual photoreceptors take light input from the eye and turn this into an electrical impulse that is then sent through the optic nerve. Many of these cells continue to the visual center of the brain in the occipital lobe but some of the neurons traverse to the Suprachiasmatic nucleus (SCN) within the hypothalamus. The SCN serves as the main controller of the circadian rhythm in humans through the expression of "clock genes". These "clock genes" transcribe various proteins that result in control of multiple behavioral and physiological rhythms including locomotion, sleep-wake cycles, thermoregulation, cardiovascular function, and many endocrine processes.

Additional hypocretin-producing neurons in the lateral hypothalamus respond to the nutritional status of the organism and light cues from the SCN to stimulate alertness, appetite, and feeding behaviors. Disturbances of these cycles can result in abnormalities of metabolism that lead to obesity and metabolic syndrome (diabetes type II, hyperlipidemia, and hypertension).

A multi-synaptic pathway utilizing the sympathetic nervous system from the SCN to the pineal gland controls release of melatonin from the pineal gland. Melatonin is derived from serotonin which itself is derived from the amino acid tryptophan. Melatonin is directly involved in the regulation of the circadian rhythm but also has a key role in the reproductive physiology of mammals. Specific effects include changes in sperm count, changes in progesterone, estradiol, luteinizing hormone, and thyroid levels. Melatonin can also inhibit sex drive and alter menstruation. Photoperiod directly correlates to melatonin release and the resulting timing of breeding season in mammals. Melatonin also affects the sleep-wake cycle, can decrease motor activity, lower body temperature, and induce fatigue.

Regulation and release of other hormones from the hypothalamus and pituitary can also be affected by complex pathways that involve the SCN. The hypothalamus releases hormones that travel down the pituitary stalk to the pituitary gland. These hormones then cause release or inhibition of pituitary hormones. Pituitary hormones then express their effect widely throughout the body. Examples of hypothalamic and pituitary hormones are shown in Table 1 below:

TABLE 1

| Hypothalamic Hormones | Pituitary Hormones |
|---|---|
| Corticotropin-releasing hormone | Adrenocorticotropic hormone (ACTH) |
| Corticotropin-releasing hormone | Melanocyte-stimulating hormone |
| Corticotropin-releasing hormone | Endorphins |
| Growth hormone releasing hormone | Growth hormone |
| Gonadotropin-releasing hormone | Luteinizing hormone (LH) and follicle-stimulating hormone (FSH) |
| Thyrotropin-releasing hormone | Thyroid-stimulating hormone (TSH) |
| Prolactin-releasing factors (serotonin, acetylcholine, opiates, & estrogens) | Prolactin |
| Somatostatin | Inhibits release of growth hormone |
| Prolactin-inhibiting factors (dopamine) | Inhibits release of prolactin |

Table 2 below describes the effects of the hormones listed in Table 1:

TABLE 2

| Hormone | Effect |
|---|---|
| ACTH | Stimulates cortisol which increases blood sugar, suppress the immune system, and affects metabolism of fat, protein, and carbohydrates |
| Melanocyte-stimulating hormone | Stimulates production and release of melanin in skin and hair, suppresses appetite, contributes to sexual arousal |
| Endorphins | Inhibits transmission of pain signals, produces feeling of euphoria |
| Growth hormone | Promotes cell growth and reproduction, cell regeneration, raises glucose and fatty acids, stimulates production of IGF-1 |
| LH & FSH | Triggers ovulation, stimulates production of testosterone, regulation of menstrual cycle, production of sperm |
| TSH | Stimulates release of thyroid hormone from the thyroid gland which affects basal metabolic rate, impacts body temp and vascular dilatation, affects growth and brain development, sexual function, sleepy, thought patterns |
| Prolactin | Milk production in females, also plays a role in metabolism, immune system regulation, and pancreatic development |
| Somatostatin | Inhibits release of growth hormone |

Melatonin (N-acetyl-5-methoxytryptamine) is a major regulatory component of the circadian rhythm produced in the pineal gland by the amino acid, tryptophan, via a series of hydroxylation and methylation reactions. In response to reduced light, by night-time, a melatonin secretion signal is sent by the optic nerve to the pineal gland which boosts melatonin production. Upon production, melatonin is secreted into the bloodstream and carried throughout the body. See Cassone, V M, et al. "Melatonin, the Pineal Gland, and Circadian Rhythms." *Journal of Biological Rhythms.*, U.S. National Library of Medicine, 1993, www.ncbi.nlm.nih.gov/pubmed/8274765. "The Human Suprachiasmatic Nucleus HHMI's BioInteractive." *HHMI BioInteractive*, www.hhmi.org/biointeractive/human-suprachiasmatic-nucleus. Mure, L S, et al. "Melanopsin-Dependent Nonvisual Responses: Evidence for Photopigment Bistability in Vivo." *Journal of Biological Rhythms.*, U.S. National Library of Medicine, October 2007, www.ncbi.nlm.nih.gov/pubmed/17876062. Musio, Carlo. "NON-VISUAL PHOTORECEPTION in INVERTEBRATES." *Non-Visual Photoreception in Invertebrates*, photobiology.info/Musio.html. *The Pineal Gland and Melatonin*, Richard Bowen, www.vivo.colostate.edu/hbooks/pathphys/endocrine/otherendo/pineal.html. Sargis, Robert M. "An Overview of the Pineal Gland." Endocrine Web, www.endocrineweb.com/endocrinology/overview-pineal-gland. Srour, Marc. "Photoreception in Animals." *Teaching Biology*, 23 Jan. 2018, bioteaching.com/photoreception-in-animals/. Welt, Corrine. "Hypothalamic—Pituitary Axis." *UpToDate*, April 2017, www.uptodate.com/contents/hypothalamic-pituitary-axis.

Follicle-stimulating hormone (FSH) is a gonadotropin, a glycoprotein polypeptide petuitary hormone. The hormone is synthesized and secreted by the gonadotropic cells of the anterior pituitary gland, and has been found to regulate the development, growth, pubertal maturation, and reproductive processes of the body. See *"Follicle-Stimulating Hormone". WebMD.*

Luteinizing hormone is a pituitary hormone produced by gonadotropic cells in the anterior pituitary gland. In females, a rise in the hormone has been found to trigger ovulation as well as the development of the corpus luteum. In males, the hormone has been found to stimulate 1 production of testosterone. See ˆ Ujihara M, Yamamoto K, Nomura K, Toyoshima S, Demura H, Nakamura Y, Ohmura K, Osawa T (June 1992). *"Subunit-specific sulphation of oligosaccharides relating to charge-heterogeneity in porcine lutrophin isoforms". Glycobiology.* 2 (3): 225-31. doi:10.1093/glycob/2.3.225. PMID 1498420.

Corticotropin-releasing hormone (CRH) is a 41-amino acid peptide derived from a 196-amino acid preprohormone. CRH is secreted by the hypothalamus in response to stress. Increased CRH production has been observed to be associated with Alzheimer's disease and major depression, and autosomal recessive hypothalamic corticotropin deficiency has multiple and potentially fatal metabolic consequences including hypoglycemia. In addition to being produced in the hypothalamus, CRH is also synthesized in peripheral tissues, such as T lymphocytes, and is highly expressed in the placenta. In the placenta, CRH is a marker that determines the length of gestation and the timing of parturition and delivery. A rapid increase in circulating levels of CRH occurs at the onset of parturition, suggesting that, in addition to its metabolic functions, CRH may act as a trigger for parturition. See *Entrez Gene: CRH corticotropin releasing hormone".*

The posterior pituitary also functions by releasing hormones synthesized in the hypothalamus. These hypothalamic neurons produce hormones that are mobilized down the axon of the cell and terminate in the posterior pituitary. The main neurohypophysial hormones and their effect are shown in Table 3:

TABLE 3

| Vasopression | Anti-diuretic action on the kidney, mediates vasoconstriction of the peripheral vessels |
|---|---|
| Oxytocin | Mediates contraction of the smooth muscle of the uterus and mammary glands |

Given the photoreceptive pathways discussed above, extraocular photoreceptors, as well as the many complex interactions that involve the hypothalamus (pituitary, brain stem, autonomic nervous system, and peripheral endocrine feedback), a number of hormones, including those in Tables 1, 2 and 3 as well as those listed below, may be regulated by the methods and systems described herein through the use of pulsed photon inputs.

In addition to the hormones provided above, number of additional hormones may be regulated in mammals using the methods and systems provided herein, including but not limited to:

A. Amino acid derived hormones such as epinephrine, triidothuyronine and thyroxine.

B. Eicosanoid hormones such as but not limited to leukotrienes.

C. Peptide hormones such as but not limited to amylin, insulin, insulin-like growth factor, and parathyroid hormone.

D. Steroid hormones such as testosterone, estradiol and progesterone.

Determination of Hormone Concentrations in Mammals

There are various analytical techniques used to determine hormone concentration in mammals, such as melatonin, including but not limited to enzyme immunoassay (ELISA), high-performance liquid chromatography (HPLC) and gas chromatography mass spectrometry (GC-MS).

Enzyme immunoassay (ELISA) kits have been developed to determine melatonin concentrations for many biological samples including *Homo sapiens*. ELISA involves detection of an analyte which is a specific substance whose presence is being quantitatively analyzed. In ELISA, a sample is added onto a stationary phase that contain specific binding properties. Multiple liquid reagents are sequentially added, incubated and washed followed by an enzymatic reaction that produces an optical change in the final liquid in the well from which the concentration of the analyte is measured. The samples are qualitatively measured with the detection through light transmittance by spectrophotometry. This involves quantifiable transmission of some specific wavelength of light through the sample and well plate. The detection sensitivity depends on the signal amplification during the chemical reactions. Enzymes that are linked to the detection reagents generate the signal which allow accurate quantification.

High-performance liquid chromatography or HPLC may also be used to determine hormone concentrations in mammals. HPLC is a technique in analytical chemistry used to separate, identify, and quantify each component in a mixture. It relies on pumps to pass a pressurized liquid solvent containing the sample mixture through a column filled with a solid adsorbent material. Each component in the sample interacts slightly differently with the adsorbent material, causing different flow rates for the different components and leading to the separation of the components as they flow out the column. HPLC has been used for manufacturing (e.g. during the production process of pharmaceutical and biological products), legal (e.g. detecting performance enhancement drugs in urine), research (e.g. separating the components of a complex biological sample, or of similar synthetic chemicals from each other), and medical (e.g. detecting vitamin D levels in blood serum) purposes. See Gerber, F.; Krummen, M; Potgeter, H.; Roth, A.; Siffrin, C.; Spoendlin, C. (2004). *"Practical aspects of fast reversed-phase high-performance liquid chromatography using 3 μm particle packed columns and monolithic columns in pharmaceutical development and production working under current good manufacturing practice"*. Journal of Chromatography A. 1036 (2): 127-133. doi: 10.1016/j.chroma.2004.02.056. PMID 15146913.

Gas chromatography-mass spectrometry (GC-MS) is an analytical method that combines the features of gas-chromatography and mass spectrometry to identify different substances within a test sample. See O. David Sparkman; Zelda Penton; Fulton G. Kitson (17 May 2011). *Gas Chromatography and Mass Spectrometry: A Practical Guide.* Academic Press. ISBN 978-0-08-092015-3.

Hormone Regulation in Mammals Through Stimulation of Opsins

An embodiment herein includes the regulation of hormones in a mammals through the emission of one or more repetitive modulated photon pulse groups within a photon signal to the mammal, where each repetitive pulse group has individual color spectrums or ranges of color spectrums, including blue, green and/or red spectrums, at a frequency, intensity and duty cycle, which can be customized, monitored and optimized for the specific hormone to be regulated in the mammal while minimizing energy used in the system. By supplying control over the rates and efficiencies of modulated photon energy to the mammal, different parts of the photostimulation of the mammal's opsins located in the hypothalamus and the retina (such as red opsins and green opsins) photo receptors are maximized allowing for regulation of hormones, including an increase in the production of specific hormones from 0.1% 10%, 20%, 50%, 100%, 150%, 200%, 250%, 500% and 1000% or greater and all integers in between, over the base line hormone level of a mammal, a decrease in the production of specific hormones from 0.1% 10%, 20%, 50%, 100%, 150%, 200%, 250%, 500% and 1000% or less and all integers in between, under the base line hormone level of a mammal as in the mammal, as well as regulation or control of a mammal mood by reducing stress or calming the mammal.

Opsins are a type of membrane bound phytochrome receptors found in the retina and the hypothalamus region of the brain of mammals. Opsins mediate a variety of functions in mammals, including hormone production, through the conversion of photons of light into an electrochemical signal.

In dairy cattle, the pineal gland is involved in synthesizing and secreting the hormone melatonin. This synthesis is initiated in mammals via light information received in the suprachiasmatic nuclei via the retinohypothalmic tract. Melanopsin, which is a photopigment, is thought to play an important role in this light signaling cascade. Melanopsin is in ganglion cells such as rods and cones and is also found throughout many of the structures in the brain. Melanopsin photoreceptors have a peak light absorption at 480 nanometers. Additionally, studies have shown that when melanopsin is pre-stimulated with 620 nm light responses to 480 nm light is enhanced. This efficiency has also been proven to be wavelength, irradiance and duration dependent.

Melanopsin stimulation is thought to inhibit melatonin production by the pineal gland. Melatonin production is directly related to milk production in dairy cows as it is an inhibitor to prolactin, the hormone responsible for milk production. Studies have shown that cows which are between milk production cycles which have higher melatonin levels will produce more milk when brought back into a production cycle. Low melatonin levels are also important during the milk production cycle as it allows for maximum prolactin levels.

In an embodiment of the current disclosure, by regulating the melatonin levels in dairy cattle via alternating wavelengths of light, such as the simultaneous pulsing of near-red and far red wavelength, in an off-set pattern within a signal (such as the signal pattern shown in FIG. 13, FIG. 14 or FIG. 18), milk production in cattle can be directly controlled. This same mechanism is thought to exist in all mammalian species.

Melatonin is also an important element of a mammal's sense of photoperiod which is directly hormonally tied to the ovulation cycle of the animal. By regulating melatonin levels in mammals via alternating wavelengths of light (such as the signal pattern shown in FIG. 13, FIG. 14 and FIG. 18) mammalian ovulation may be regulated.

Photons are massless, elementary particles with no electric charge. Photons are emitted from a variety of sources such as molecular and nuclear processes, the quantum of light and all other forms of electromagnetic radiation. Photon energy can be absorbed by phytochromes in living mammals and convert it into an electrochemical signal which manipulates a metabolite.

This phenomenon can be seen in the vision opsin chromophore in humans. The absorption of a photon of light results in the photoisomerisation of the chromophore from the 11-cis to an all-trans conformation. The photoisomerization induces a conformational change in the opsin protein, causing the activation of the phototransduction cascade. The result is the conversion of rhodopsin into prelumirhodopsin with an all-trans chromophore. The opsin remains insensitive to light in the trans form. The change is followed by several rapid shifts in the structure of the opsin and also changes in the relation of the chromophore to the opsin. It is regenerated by the replacement of the all-trans retinal by a newly synthesized 11-cis-retinal provided from the retinal epithelial cells. This reversible and rapid chemical cycle is responsible for the identification and reception to color in humans. Similar biochemical processes exist in mammals. Phytochromes and pheophytins behave very similarly to opsins in that they can be rapidly regulated to switch between the cis and trans configurations by dosing with differing wavelengths of light.

The responses of mammals to the variations in the length of day and night involve photon absorption molecular changes that closely parallel those involved in the vision cycle in humans.

Mammal responses to a photon signal with one or more specific photon modulations may be monitored depending upon the desired hormone to be regulated. When the desired hormone is the production of melatonin, the mammal may be monitored for the stimulation of the pineal gland for the expression or release of melatonin or the release of luteinizing hormones, a heterodimeric glycoprotein to indicate impending ovulation in female mammals. Melatonin or luteinizing hormones may be monitored via blood or urinary samples. Samples may be taken daily or at various times during the day to identify the mammal reaction to the photon modulation to ensure efficient ovulation, or milk production.

The present disclosure also provides methods and systems for the amount of electric power used in the process of mammal hormone production, where the amount of energy delivered can be defined by calculating the total area under the graph of power over time. The present disclosure further provides methods and systems that allow for the monitoring, reporting and control of the amount of electric power used to regulate a desired hormone in a mammal, allowing an end user or energy provider to identify trends in energy use.

An embodiment of the system of the present disclosure comprises at least one photon emitter with at least one photon source, such as an LED or array of LEDs in communication with a photon emission modulation controller, including but not limited to a digital output signal, a solid-state relay or field effect transistor BJT, or FET, or power converter. Photon emitters are modulated to send a repetitive pulse of photons, where each individual pulse comprises at least one color spectrum, wavelength or multiple color spectrums or wavelengths and is capable varying intensities. Each photon pulse is directed toward a mammal for a duration of time ON, such as two milliseconds with one or more intensities, with a duration of delay or time OFF between photon pulses, such as two hundred milliseconds or up to 24 hours.

As used herein, "mammal" includes warm-blooded, vertebrates possessing hair and mammary glands, including but not limited to mammals from the orders primates including but not limited to humans, ungulates, including but not limited to cattle, horses, camels, pigs, deer, elk, alpacas, lamas, and moose, carnivores, including but not limited to bears, the weasel family, dogs, cats, wolves, lions, tigers, skunks, rodents, including but not limited to rats, mice, and beaver, chiropteras, including but not limited to bats, marsupials, including but not limited to kangaroos and opossums and cetacean, including, whales and dolphins.

As used herein, "duty cycle" is the length of time it takes for a device to go through a complete ON/OFF cycle or photon signal. Duty cycle is the percent of time that an entity spends in an active state as a fraction of the total time under consideration. The term duty cycle is often used pertaining to electrical devices, such as switching power supplies. In an electrical device, a 60% duty cycle means the power is on 60% of the time and off 40% of the time. An example duty cycle of the present disclosure may range from 0.01% to 90% including all integers in between.

As used herein "frequency" is the number of occurrences of a repeating event per unit time and any frequency may be used in the system of the present disclosure. Frequency may also refer to a temporal frequency. The repeated period is the duration of one cycle in a repeating event, so the period is the reciprocal of the frequency.

As used herein, the term "waveform" refers to the shape of a graph of the varying quantity against time or distance.

As used herein, the term "pulse wave" or "pulse train" is a kind of non-sinusoidal waveform that is similar to a square wave, but does not have the symmetrical shape associated with a perfect square wave. It is a term common to synthesizer programming and is a typical waveform available on many synthesizers. The exact shape of the wave is determined by the duty cycle of the oscillator. In many synthesizers, the duty cycle can be modulated (sometimes called pulse-width modulation) for a more dynamic timbre. The pulse wave is also known as the rectangular wave, the periodic version of the rectangular function.

In an embodiment of the present disclosure and as will be described in further detail below, the emission of one or more repetitive photon pulses within a photon signal from the growth system described herein where each repetitive photon pulse has a duration ON with one or more intensities and a duration OFF, a wavelength band and duty cycle induce a gain efficiency greater than 1 where Gain=Amplitude out/Amplitude in.

FIG. 1 provides a block diagram showing an example of a photon modulation management system 100 for use in the regulation of hormones in mammals. As shown in FIG. 1, a photon emitter 106, 108, 110, 112, 114 and 116 is shown over a period of time in communication with a photon emission modulation controller 104 for the purpose of modulating the emission of photons to a mammal for stimulating opsins in order to regulate hormone production as well as to control the animals stress and mood. The modulated application of photons to a mammal by providing photon pulses of one or more frequencies followed by pulses of one or more other frequencies for a duration along with a delay between pulses, allows for peak stimulation/modulation of a mammals biological components (opsins receptors) and biological responses, including hormone production such as the pulsing of one or more specific spectrums of light to induce a specific electrochemical signal for the production of a specific hormone or the pulsing of two or more specific wavelengths within a signal, (such as the signal pattern shown in FIGS. 13-19) to produce a specific hormone, allowing for an increase in the production of specific hormones from 0.1%, 1.0%, 5%, 7.5, 10%, 12.2%, 20%, 33.3%, 50%, 81.7%, 100%, 143.9%, 150%, 181.4%, 200%, 250%, 444.2%, 500% and 5000% or greater and all integers in between, over the baseline hormone level of a mammal, or a decrease in the production of specific hormones from 0.1%, 1.2%, 7.7%, 10%, 15.6, 20%, 47.2%, 50%, 74.5%, 100%, 150%, 200%, 250%, 500% and 5000% or less and all integers in between, under the baseline hormone level of a mammal as in the mammal, along with regulation or control of a mammal's mood by reducing stress or calming the mammal. Further the modulation of photons to a mammal allows for the optimization of photon absorption by opsin receptors without oversaturation of the mammal's receptors. As described below, the modulation of the photon pulses increases energy and heat efficiency of current dairy production lighting systems by reducing the overall power draw by the system of the present disclosure as much as 99% or more of the photon source when compared to conventional beef or dairy production lighting systems, such as a 60 watt light, thereby reducing the amount of power and cost used to facilitate hormone production in a mammal. In an example of the energy saving potential of the system of the present disclosure, the system pulses 49.2 watts of photons for two microseconds per 200 microseconds creating an effective power consumption of 0.49 watt-hrs/hr on the power payment meter or 0.82% of the power in a 60-watt standard incandescent bulb. In addition, because the photon emitter is not continuously emitting photons, the amount of heat produced from the photon emitter will be significantly reduced, thereby significantly reducing the cost of cooling a facility to compensate for the increased heat from lighting. The system of the present disclosure may be customized based upon mammal specific requirements for photon intensity, pulse ON duration, pulse OFF (or duty cycle), the light spectrum of the pulse including but not limited to white, near-red, yellow, green, and blue, orange, far-red, infrared, and ultra-violet to encourage optimal hormone production as well as the control of the animal's stress and mood.

As shown in FIG. 1, a master logic controller (MLC) 102, such as solid-state circuit with digital output control or a central processing unit (CPU) is in communication with a photon emission modulation controller 104 by means of a communication signal 134. The MLC 102 provides the system of the present disclosure with input/output of the parameters and the appropriate instructions or the specialized functions for the modulation of photons within a signal from a photon emitter 106 and 108.

In a further embodiment, the MLC 102 may be hard wired or wireless to an external source such as a host, allowing external access to the MLC 102 by a host. This allows remote access by a user to monitor the input and output of the MLC 102, provide instructions or control to the systems while also allowing for remote programming and monitoring of the MLC 102.

In a further embodiment, a power measurement or power consumption sensor may be integrated or embedded into the MLC 102 in the form of an integrated circuit allowing for the measurement and reporting of the power consumption of the system based on the voltage and the current draw of the system of the present disclosure. The power consumption of the system can then be communicated either wirelessly or by hardwire from the MLC 102 to a host. Data, including power consumption may also be sent to an outside receiver such as a database that is not connected to the system.

The photon emission modulation controller 104 receives commands and instructions from the MLC 102 including but not limited to the duration ON and intensity, duration OFF duty cycle, intensity, wavelength band and frequency of each repetitive photon pulse within a photon signal 118 from a photon emitter 106. The photon emission modulation controller 104 may be any device that modulates the quanta and provides the control and command for the duration ON and intensity, duration OFF, wavelength band and frequency of each repetitive photon pulse from a photon emitter 106 and 108. A variety of devices may be used as the photon emission modulation controller 104, including but not limited to a solid-state relay (SSR), such as the Magnacraft 70S2 3V solid-state relay from Magnacraft Inc., optical choppers, power converters and other devices that induce modulation of a photon pulse. A variety of photon emitters 106 and 108 may be used, including but not limited to, an incandescent (Tungsten-halogen and Xenon), Fluorescent (CFL's), high intensity discharge (Metal Halide, High-Pressure Sodium, Low-Pressure Sodium, Mercury Vapor), sunlight, light emitting diodes (LEDs). It should be understood that this description is applicable to any such system with other types of photon emission modulation controllers, including other methods to cycle a light or photon source ON and OFF, cycling one or more colors or spectrums of light at different times, durations and intensities, such as near-red, green, blue and far-red, allowing multiple pulses of one spectrum before pulsing another spectrum, as will be understood by one skilled in the art, once they understand the principles of the embodiments.

As shown in FIG. 1, based on the instructions from the MLC 102, the photon emission modulation controller 104 sends a photon emission control signal 136 to a photon emitter 106. When the photon emission control signal 136 is sent to the photon emitter 106 goes ON, the photon emitter 106 emits at least one photon signal 118 where each photon signal comprises one or more repetitive photon pulses, where each repetitive photon pulse has separate duration ON with one or more intensities, a wavelength band and frequency, which is transmitted to a mammal 122. Then based on the instructions from the MLC 102, when the photon emitter control signal 136 sent to the photon emitter 108 goes OFF, the photon emitter 108 will not emit a photon pulse, and therefore no photons are transmitted to a mammal 122. As shown in FIG. 1, starting from the left side of FIG. 1, the emission of photons 118, such as a pulse of near-red photons, and mammal 122 hormone production 124 is shown over a period of time 120. The example of FIG. 1 provides a photon signal 118, such as ultraviolet, violet, near-red, green, yellow, orange, blue and far-red, allowing multiple pulses of one spectrum before pulsing another spectrum or in combination, as will be understood by one skilled in the art, once they understand the principles of the embodiments. It should also be understood that this ON and OFF cycling can be in the form of a digital pulse, pulse train, or varying waveform.

As will be understood by one skilled in art, in an additional embodiment, the system for use in the regulation of hormones as described in FIG. 1 may be completely housed in a single unit comprising multiple photon emitters creating an array (shown in FIG. 3, FIG. 7, FIGS. 8a, 8b, 8c, 8d, and FIG. 9), allowing each individual single unit to be self-sufficient, without the need for an external control or logic unit. An example self-sufficient unit with multiple photon emitters may be in the form of a unit that may be connected to a light socket, or light fixtures that may be suspended above one or more mammals and connected to a power source.

The systems as shown in FIG. 1 may also take the form of a master/slave system, as will be discussed in FIG. 4, where by example, a master photon emitter containing all logic and controls for the emission of photon from master photon emitter as well as any additional photon emitters in communication with the master photon emitter.

Figure 2:
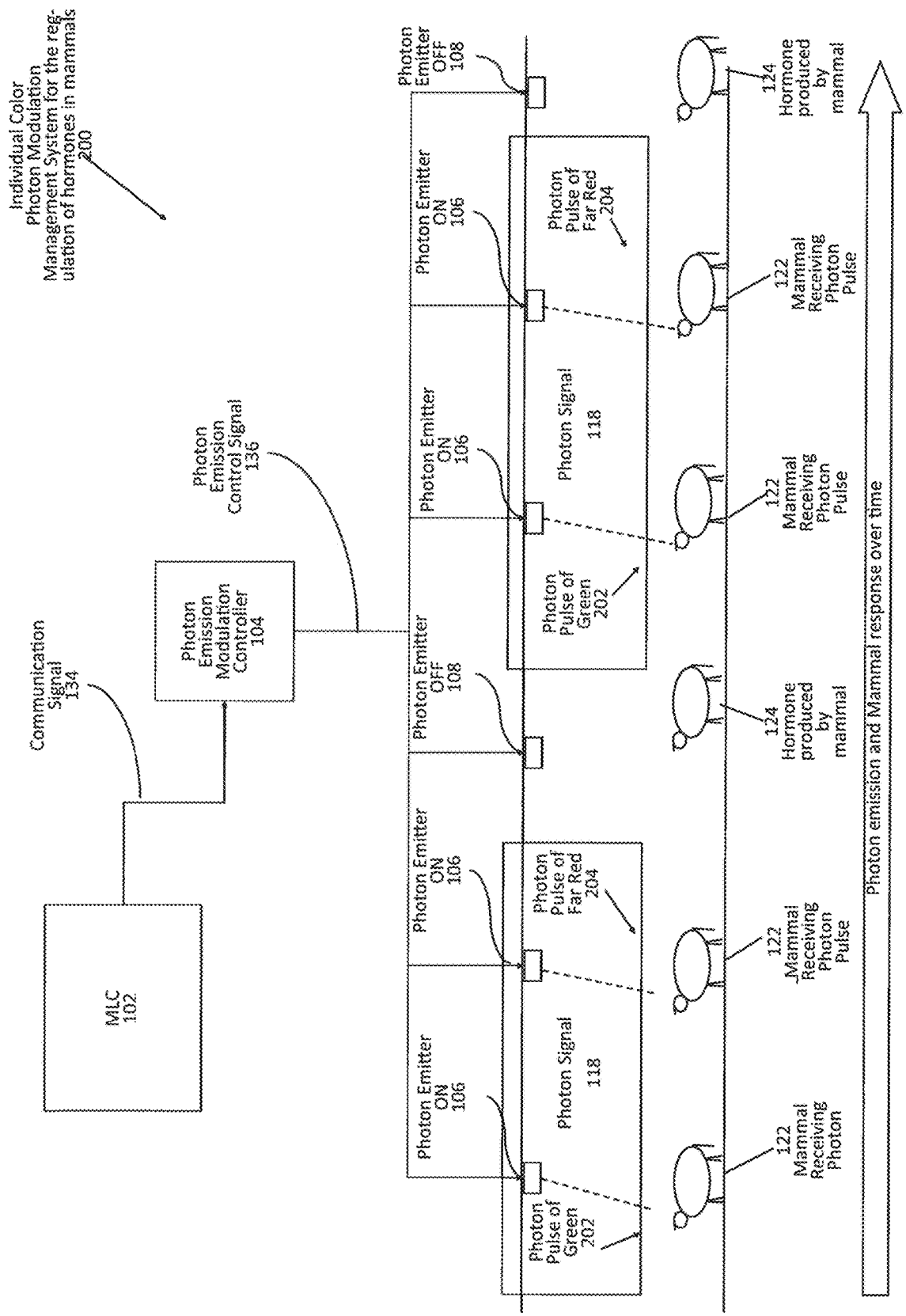
FIG. 2 is a diagram showing an example of an individual color photon modulation growth system pulsing different specific wavelengths of light to regulate hormone production in a mammal.

The systems as shown in FIG. 1 and FIG. 2 may also take the form of a synchronized series of lights or daisy chain of lights, where by example, two of more photon emitters are in communication with each other to synchronize the emission of signals with two or more components. To clarify, each photon emitter will individually emit a signal comprising at least two components, however the system, by example, through commands from a master logic controller, will allow for the emission of signals from the series of emitters to be synchronized.

A variety of power supplies may be used in the present disclosure. These sources of power may include but are not limited to battery, converters for line power, solar and/or wind power. The intensity of the photon pulse may be static with distinct ON/OFF cycles or the intensity may be changes of 5% or larger of the quanta of the photon pulse. The intensity of the photon pulse from the photon emitter can be controlled through the variance of voltage and/or current from the power supplies and delivered to the light source. It will also be appreciated by one skilled in the art as to the support circuitry that will be required for the system of the present disclosure, including the photon emitter control unit and the photon emitters. Further, it will be appreciated that the configuration, installation and operation of the required components and support circuitry are well known in the art. The program code, if a program code is utilized, for performing the operations disclosed herein will be dependent upon the particular processor and programming language utilized in the system of the present disclosure. Consequently, it will be appreciated that the generation of a program code from the disclosure presented herein would be within the skill of an ordinary artisan.

FIG. 2 provides a block diagrams showing an example of a photon modulation management system 200 for the regulation of hormones in a mammal. As shown in FIG. 2 and repeated from FIG. 1, a photon emitter 106 and 108 is shown over a period of time in communication with a photon emission modulation controller 104 for the purpose of modulating individual pulses of photons comprising individual color spectrums to a mammal (not shown), including but not limited to white, green, near-red, blue, yellow orange, far-red, infrared, and ultra-violet color spectrums, wavelength between 0.1 nm and 1 cm. As will be understood by one skilled in the art, the present disclosure may include color spectrums of specific, individual wavelengths between 0.1 nm and 1.0 cm, or may include a range or band of wavelengths 0.1 to 200 nm in width, herein "wavelength band."

The modulation of individual color spectrums of photons to a mammal by providing specific color spectrum pulses for a duration along with a delay between pulses (examples are shown in FIGS. 13-19), allows for peak stimulation of a mammal's biological components and responses, such as a mammal's retina opsins and hypothalamus opsins for ovulation, pineal gland to regulation hormone production. This peak stimulation allows for the regulation of hormones by increasing the production of specific hormones from 0.1%, 1.0%, 5%, 7.5, 10%, 12.2%, 20%, 33.3%, 50%, 81.7%, 100%, 143.9%, 150%, 181.4%, 200%, 250%, 444.2%, 500% and 1000% and all integers in between, over the baseline hormone level of a mammal, or decreasing the production of specific hormones from 0.1%, 1.2%, 7.7%, 10%, 15.6, 20%, 47.2%, 50%, 74.5%, 100%, 150%, 200%, 250%, 500% and 1000% and all integers in between, under the baseline hormone level of a mammal as in the mammal, along with regulation or control of a mammal's mood by reducing stress or calming the mammal.

Examples of the ability to control specific aspects of a mammal biological components or responses through the pulsing of individual color spectrums, specific color wavelength or a range of color wavelengths may include but are not limited to:

a. milk production in mammals through the modulation of pulses when melanopsin is pre-stimulated with 620 nm light responses to 480 nm light is enhanced;
b. use of blue spectrum between 390 to 470 nm to treat jaundice in prenatal mammals, such as human premature babies;
c. ovulation through the modulation of pulses of a specific far-red wavelength (such as 730 nm, an example wavelength range may include 710 to 850 nm) for a period of time;
d. hunger, growth, sexual development as well as helps to control the mood of the mammals by pulses of blue light, as well as the regulation of circadian rhythms (an example range may include with a range of 450 to 495 nm);
e. ultraviolet or violet light (by example 10 nm to 450 nm) may be used to influence social behavior and mood as well as to facilitate nutrient update such as calcium; and
f. additional orange light (590 nm to 620 nm) and/or yellow light (570 nm to 590 nm) may also be used to influence mammal responses.

The modulation of individual color spectrums, specific wavelength and a range of wavelengths of photons to a mammal by providing specific color spectrum pulses for a duration along with a delay between pulses also allows for the control hormone production for mood, growth, ovulation, sexual maturity, and hunger in mammal. An example may include one light or through the combination of many lights, cycling the lights on and off to control ovulation, milk production and growth in a mammal.

As shown in FIG. 2 and repeated from FIG. 1, a master logic controller (MLC) 102 is in communication with a photon emission modulation controller 104 by means of a communication signal 134. The MLC 102 provides the system of the present disclosure with input/output of the parameters and the appropriate instructions or the specialized functions for the modulation of a specific individual color spectrum of photons from a photon emitter 106 and 108.

The photon emission modulation controller 104 receives commands and instructions from the MLC 102 including but not limited to the duration ON and intensity, duration OFF, wavelength band and frequency of each repetitive photon pulse 202 and 204 within a photon signal 118 or a plurality of pulses of a specific color spectrum from a photon emitter 106 and 108 within a photon signal. The photon emission modulation controller 104 provides the control and command for the duration ON and intensity, duration OFF, wavelength band and frequency of each repetitive photon pulse 202 and 204 within a photon signal 118 or plurality of pulses from a photon emitter 106, and 108.

As shown in FIG. 2, based on the instructions from the MLC 102, the photon emission modulation controller 104 sends a photon emission control signal 136 to a photon emitter 106 and 108. When the photon emission control signal 136 sent to the photon emitter 106 ON, the photon emitter 106 emits one or more repetitive photon pulses of a specific color spectrum 202 or 204, comprising the photon signal 118, which is transmitted to a mammal 122. Then based on the instructions from the MLC 102, when the photon emitter control signal 136 sent to the photon emitter 108 goes OFF, the photon emitter 108 will not emit a photon signal, and therefore no photons are transmitted to a mammal 122. As shown in FIG. 2, starting from the left side of FIG. 2, the emission of a photon signal 118 comprising repetitive photon pulses of a specific color spectrum 202 (green) and 204 (far-red) and mammal 122 hormone production is shown over a period of time 120. The example of FIG. 2 provides a photon signal 118 with photon pulse or plurality of pulses of a green color spectrum 202 emitted from a photon emitter 106 for two (2) milliseconds, followed by a photon pulse or plurality of pulses of a far-red color spectrum 204 for a duration of two (2) milliseconds with a duration of delay of two hundred (200) milliseconds of each pulse before the photon signal repeats with a photon pulse or plurality of pulses 202 emitted from the same photon emitter 106 for two milliseconds followed by a second photon pulse or plurality of pulses of a far-red color spectrum 204 for a duration of two milliseconds from the same photon emitter 114 (please note that FIG. 2 is a descriptive example of photon pulses emitted over time. FIG. 2 is not drawn to scale and the amount of hormone production by the mammal between pulses in FIG. 2 is not necessarily to scale). Please note that the two pulses (green and far-red) within the signal 118 are pulsed simultaneously but with their durations ON and OFF offset in this example. While two photon pulses are shown in FIG. 2, as one skilled in the art will understand once they understand the invention, any number of pulses, from 1 to 15 or even more, may be within a photon signal directed to an organism.

The system of the present disclosure as described in FIGS. 1 and 2 allows for the regulation and control of the production of various hormones in a mammal through the cycling of one or more colors or spectrums of light at different times, durations and intensities, such as near-red, green, blue and far-red, allowing single pulses or multiple pulses of one spectrum with a delay before pulsing another spectrum (examples shown in FIGS. 13-19). The pulsing of individual color spectrums in unison or individually offset for a duration with a delay between pulses within a signal allows for increased efficiency in the stimulation of opsins for hormone regulation and production.

A variety of sources or devices may be used to produce photons from the photon emitters, many of which are known in the art. However, an example of a device or sources suitable for the emission or production of photons from a photon emitter include an LED, which may be packaged within an LED array designed to create a desired spectrum of photons. While LEDs are shown in this example, it will be understood by one skilled in the art that a variety of sources may be used for the emission of photons including but not limited to metal halide light, fluorescent light, high-pressure sodium light, incandescent light and LEDs. Please note that if a metal halide light, fluorescent light, high-pressure sodium light, incandescent light is used with the methods, systems and apparatuses described herein, the proper use of these forms of photon emitters would be to modulate and then filter the light to control what wavelength for what duration is passed through.

Embodiments of the present disclosure can apply to LEDs having various durations of photon emissions, including durations of photon emissions of specific color spectrums and intensity. The pulsed photon emissions of specific color spectrums within a photon signal may be longer or shorter depending on the mammal in question, the age of the mammal and how the emission will be used in facilitating the regulation of hormones and control of stress or mood.

The use of an array of LEDs may be controlled to provide the optimal photon pulse of one or more color spectrums for specific mammal ovulation, milk production and growth such as in beef. The user may simply select the photon pulse intensity, color spectrum, frequency and duty cycle for a particular type of mammal to encourage efficient biological responses in mammals. LED packages can be customized to meet each mammal's specific requirements. By using packaged LED arrays with the customized pulsed photon emission, as discussed above, embodiments described herein may be used to control light to alter the mammal weight, and sexual maturity within the target mammal.

Figure 3:
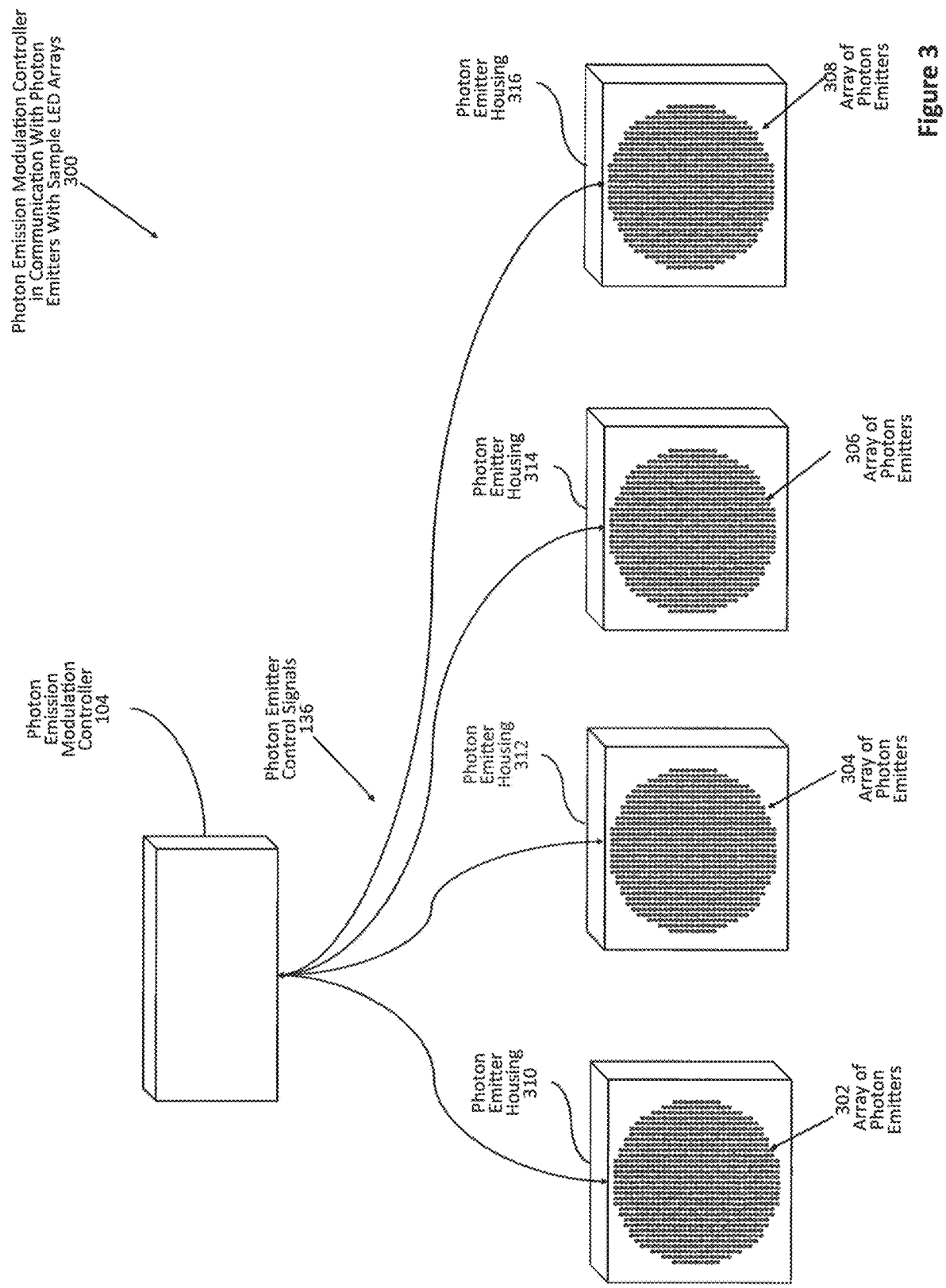
FIG. 3 is a diagram showing a photon emission modulation controller in communication with a plurality of photon emitters with sample LED arrays.

FIG. 3 is a diagram of an example of a plurality of photon emitters with LED arrays 300 as the source of photons from the photon emitter. As shown in FIG. 3, a photon emission modulation controller 104 is in communication by means of a plurality of photon emitter control signals 136 with a plurality of photon emitters. As further shown in FIG. 3, each photon emitter comprises an array of LEDs 302, 304, 306 and 308. Each array of LEDs 302, 304, 306 and 308 and the circuitry to allow for the array of LEDs to communicate with the photon emission modulation controller 104 are contained in an LED array housing 310, 312, 314 and 316.

As shown in FIG. 3, the shape of LED array is a circle, however as will be understood by one skilled in the art, the shape of the array may take a variety of forms based upon the needed biological response of the mammal. The shape of the array may include but is not limited to, circular, square, linear, rectangular, triangular, octagonal, pentagonal and a variety of other shapes.

The LED array housing 310, 312, 314 and 316 for each photon emitter may be made of a variety of suitable materials including, but are not limited to, plastic, thermoplastic, and other types of polymeric materials. Composite materials or other engineered materials may also be used. In some embodiments, the housing may be made by a plastic, aluminum, aluminum alloy, zinc, zinc alloy, zinc, casting or injection molding manufacturing process. In some embodiments, the housing may be transparent or semi-transparent and in any color.

Figure 4:
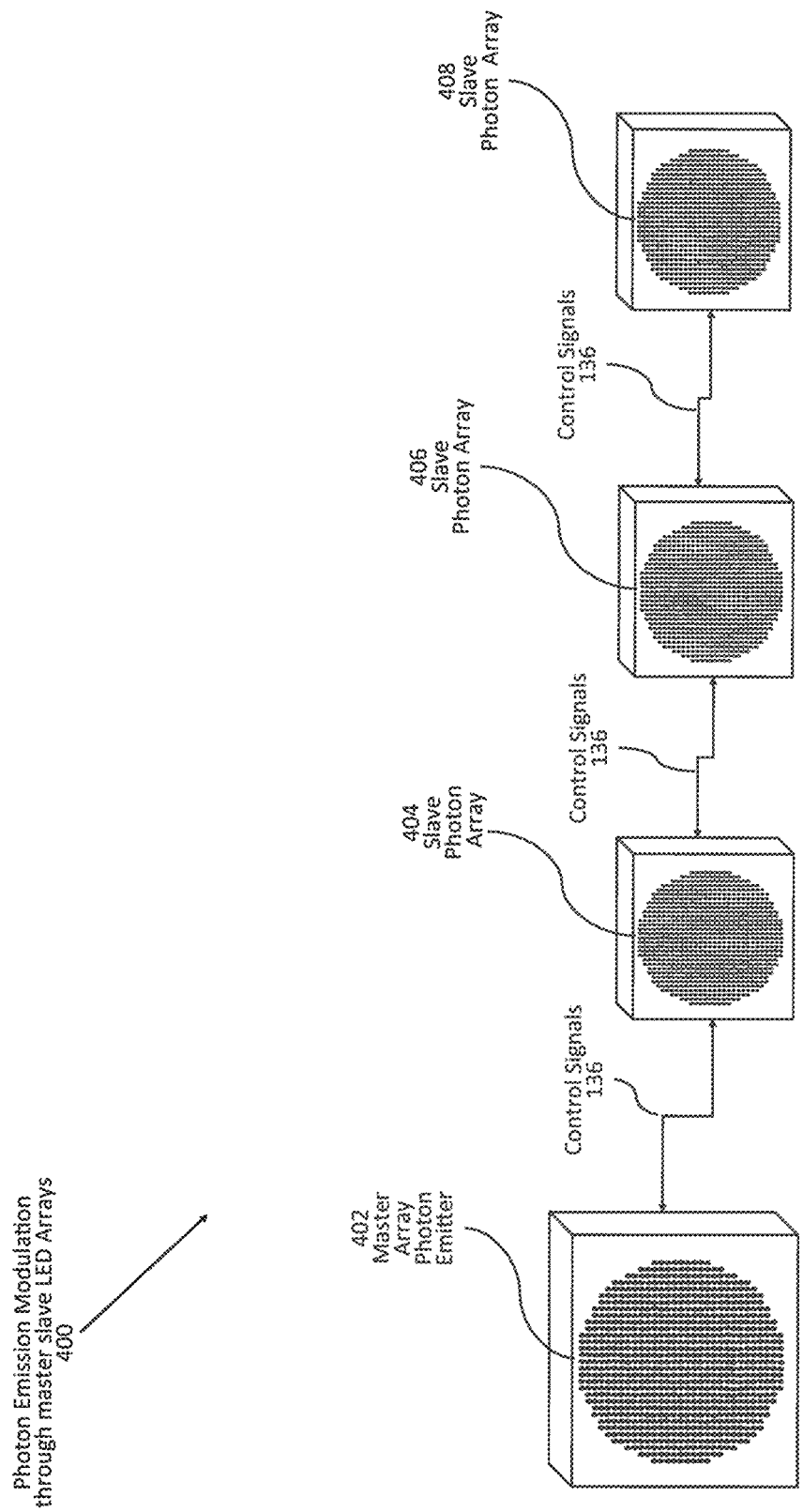
FIG. 4 is a diagram showing photon emission modulation through a master/slave LED array.

FIG. 4 is a diagram of an example of a plurality of photon emitters with a master photon emitter in communication and control of one or more slave photon emitters, 400. As shown in FIG. 4, a master photon emitter 402 is in communication by means of a photon control signal 136 with a series of slave photon emitters 404, 406, and 408. The master photon emitter 402 contains a controller, such as the MLC (102 of FIGS. 1 and 2), as well as photon emission modulation controller (shown as 104 FIGS. 1 and 2) which controls the duration ON and intensity, duration OFF, and frequency of each specific color spectrum photon pulse within each photon signal from an array of LEDs housed within the master photon emitter 402 while also allowing the master photon emitter to control the duration ON and intensity, duration OFF, and frequency of each specific color spectrum photon pulse within each photon signal from each slave photon emitters 404, 406, and 408.

Conversely, each slave photon emitter 404, 406, and 408 contains the circuitry to receive command signals 136 from the master photon emitter 402 and the circuitry necessary to emit a photon pulse of a specific spectrum from an array of LEDs (such as near-red, far-red, blue, green or orange) housed within each slave photon emitter 404, 406, and 408. For clarity, each slave photon emitter does not contain a controller such as the MLC nor does the slave photon emitter 404, 406, and 408 contain a photon emission modulation controller. All commands and controls for the slave photon emitter 404, 406, and 408 are received from the master photon emitter 402. This master/slave system allows for sharing of a single power supply and microcontroller. Master has the power supply and that power is also transferred to the slaves. Additionally, the master/slave system can be utilized to pulse photons in patterns to help regulate the production of hormones in other mammals.

A bus system (wired or wireless) may be included in MLC of the master photon emitter 402 or in each slave photon emitter 404, 406 and 408 to allow for the specific control by the master photon emitter 402 of each individual slave photon emitter 404, 406 and 408. By way of example, the master photon emitter 402 may send a signal 136 to a specific slave photon emitter 404 commanding the slave photon emitter 404 to emit photon signal with a far-red pulse for a specific duration, while the master photon emitter 402 simultaneously sends a command signal 136 to a second slave photon emitter 406 to emit a photon signal with green pulse for a specific duration. While this descriptive example shows an array, plurality or chain of three slave photon emitters 404, 406 and 408 in with a master photon emitter 402, it should be understood that this description is applicable to any such system with any number of slave photon emitters in communication and under the control of a master photon emitter, as will be understood by one skilled in the art, once they understand the principles of the embodiments.

In a further embodiment, the master photon emitter 402 may be hard wired or wireless to allow external access to the master photon emitter 402 by a host, allowing remote access to monitor the input and output of the master photon emitter 402 while also allowing for remote programming of the master photon emitter.

Figure 5:
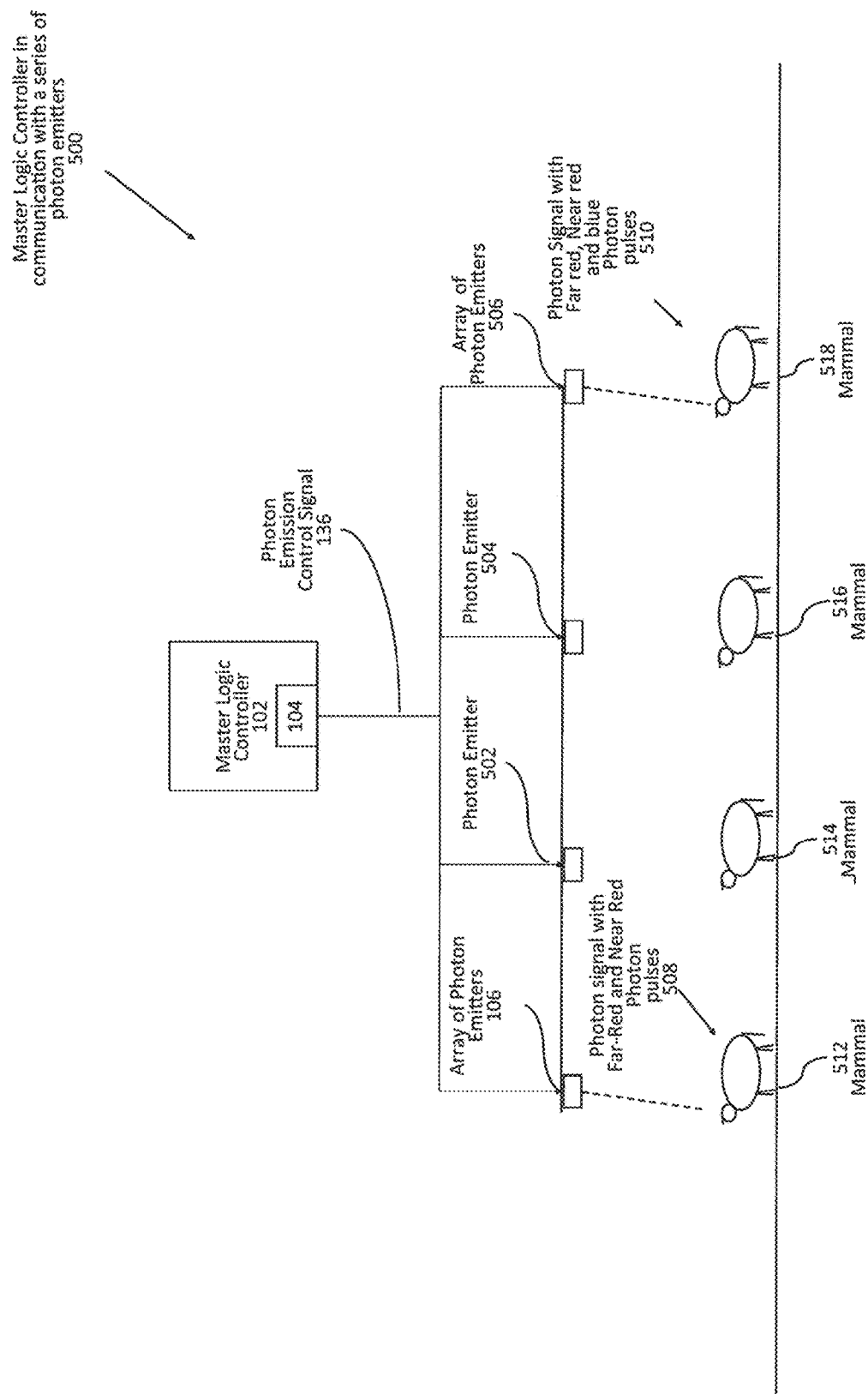
FIG. 5 is a diagram showing a master logic controller in communication and control of a series of photon emitters.

FIG. 5 is a diagram of an example of a master logic controller in communication and control of one or more photon emitters, 500. As shown in FIG. 5, a master logic controller 102 is in communication by means of a photon emission control signal 136 with a series of photon emitters 106, 502, 504 and 506 located above four different mammals 512, 514, 516 or 518. In this example, the master logic controller or MLC 102 (as previously discussed in FIGS. 1, 2 and 3) also contains a photon emission modulation controller 104 (shown discussed in FIGS. 1, 2 and 3) which allows the MLC 102 to control the duration ON and intensity, duration OFF, and frequency of each specific color spectrum photon pulse within a photon signal from an array of LEDs housed within each photon emitter 106, 502, 504 and 506.

Through the photon emission modulation controller 104, the MLC 102 communicates commands and instructions to each photon emitter 106, 502, 504 and 506 including but not limited to the duration ON, intensity, duration OFF and frequency of each specific color spectrum photon pulse within each photon signal 508 and 510 from each photon emitter 106, 502, 504 and 506. The MLC 102 also maintains control of the power supply to the system and control the transfer of power to each individual photon emitter 106, 502, 504 and 506.

As shown in FIG. 5, based on the instructions from the MLC 102, the photon emission modulation controller 104 sends a photon emission control signal 136 to each individual photon emitter 106, 502, 504 and 506. Based on the specific instructions sent to each photon emitter 106, 502, 504 and 506, individual photon emitters 106 or 506 may a photon signal comprising repetitive photon pulses of one or more specific color spectrums 508 and 510 to a mammal 512, 514, 516 or 518 (such as a photon signal with a far-red pulse and a near-red pulse 508 at various durations ON and OFF or a photon signal with pulse of far-red, a pulse of near-red and a pulse of blue at various durations ON and OFF 510). As further shown in FIG. 5, based on the instructions from the MLC 102, other individual photon emitters 502 or 504 may not emit a photon signal toward a mammal 122 for a duration.

The ability of the MLC 102 to control the photon output or emitted from each individual photon emitter 106, 502, 504 and 506 allows the system of the present disclosure to modify the photon emission to a mammal based on the specific needs or requirements for a mammal. As discussed in association with FIG. 2, by way of example, the MLC may be programmed to issue a signal to a specific emitter for modulation of pulses of far-red light for a period of time followed by pulses of blue light in combination with near-red light for the control of a biological responses in mammals and mood/hunger.

In the example shown in FIG. 5, all commands and controls for each photon emitter 106, 502, 504 and 506 are received externally from the MLC 102. However, as will be understood by one skilled in the art, the logic and hardware associated with the MLC 102 and photon emission modulation controller 104 may also be housed within each individual photon emitter, allowing each individual photon emitter to be self-sufficient, without the need for an external control or logic unit.

In a further embodiment, the MLC 102 may be hard wired or wireless, allowing external access to the MLC 102 by a user. This allows remote access by a user to monitor the input and output of the MLC 102 while also allowing for remote programming of the MLC 102.

Figure 6:
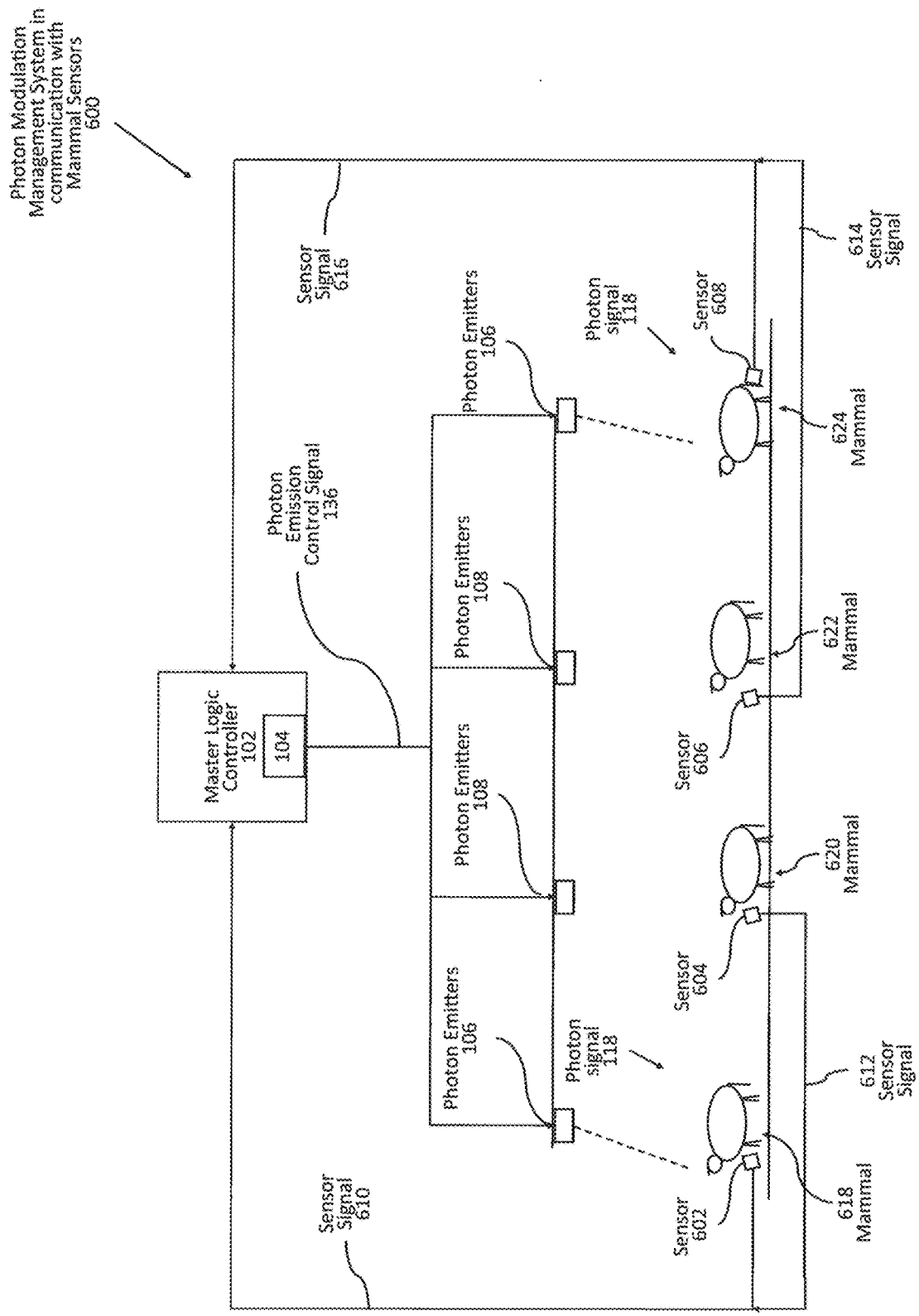
FIG. 6 is a diagram showing a photon modulation management system in communication with a series of mammal sensors.

FIG. 6 provides an example of a further embodiment, showing the photon modulation system of the present disclosure where one or more sensors are used to monitor a mammal's environmental conditions as well as the mammal's responses 600 to the photon system provided herein. As shown in FIG. 6, one or more sensors 602, 604, 606 and 608 are associated with each mammal 618, 620, 622, and 624 in order to monitor various conditions associated with the mammal 618, 620, 622, and 624. The conditions associated with the mammal, which may be monitored include but are not limited to, humidity, air temperature, volume, movement, $O_2$, $CO_2$, CO, pH, and weight. As will be understood by one skilled in the art, the sensors may include but are not limited to temperature sensor, an infrared sensor, motion sensor, microphones, gas sensors, cameras, and scales.

The sensors 602, 604, 606 and 608 monitor one or more conditions associated with the mammal 618, 620, 622, and 624 and then transmit the data 610, 612, 614 or 616 to the MLC 102. Transferring the data from the one or more sensors 602, 604, 606 and 608 to the MLC 102 can be accomplished in a number of ways, either wirelessly or hard wired. As will be understood by one skilled in art, a variety of communication systems may be used for the delivery of sensor-derived information from the mammal 618, 620, 622, and 624 to the MLC 102.

The data from the one or more sensors 602, 604, 606 and 608 is analyzed by the MLC 102. Based on the information from the sensors, the MLC 102, through the photon emission modulation controller 104, the MLC 102 is able to adjust the duration ON, intensity, duration OFF, duty cycle and frequency of each specific color spectrum photon pulse 608 and 610 of each photon signal 118 of each individual photon emitter 106, 602, 604 and 606, or to adjust the duration ON, intensity, duration OFF, duty cycle and frequency of a group of photon emitters based on the needs of the individual mammals 618, 620, 622, and 624 associated with a specific sensor 602, 604, 606 and 608 or the needs of the mammals as a whole. An example may include adjusting a signal to comprise both blue and far-red 608 at various durations or adjusting duration of a pulse of far-red, green and blue 610.

In additional embodiments, the system of the present disclosure may also include a watering system, feeding systems, environmental as well as health system (not shown in FIG. 6) in communication and under the control of the MLC 102 or a separate logic controller. Based on information from the sensors 602, 604, 606 and 608 associated with each mammal, the MLC 102 is able to communicate with a watering system, feeding system, heating and cooling systems, medication systems based upon the needs of the mammals. Data, including power can be sent to an outside receiver such as a database that is not connected to the system.

Figure 7:
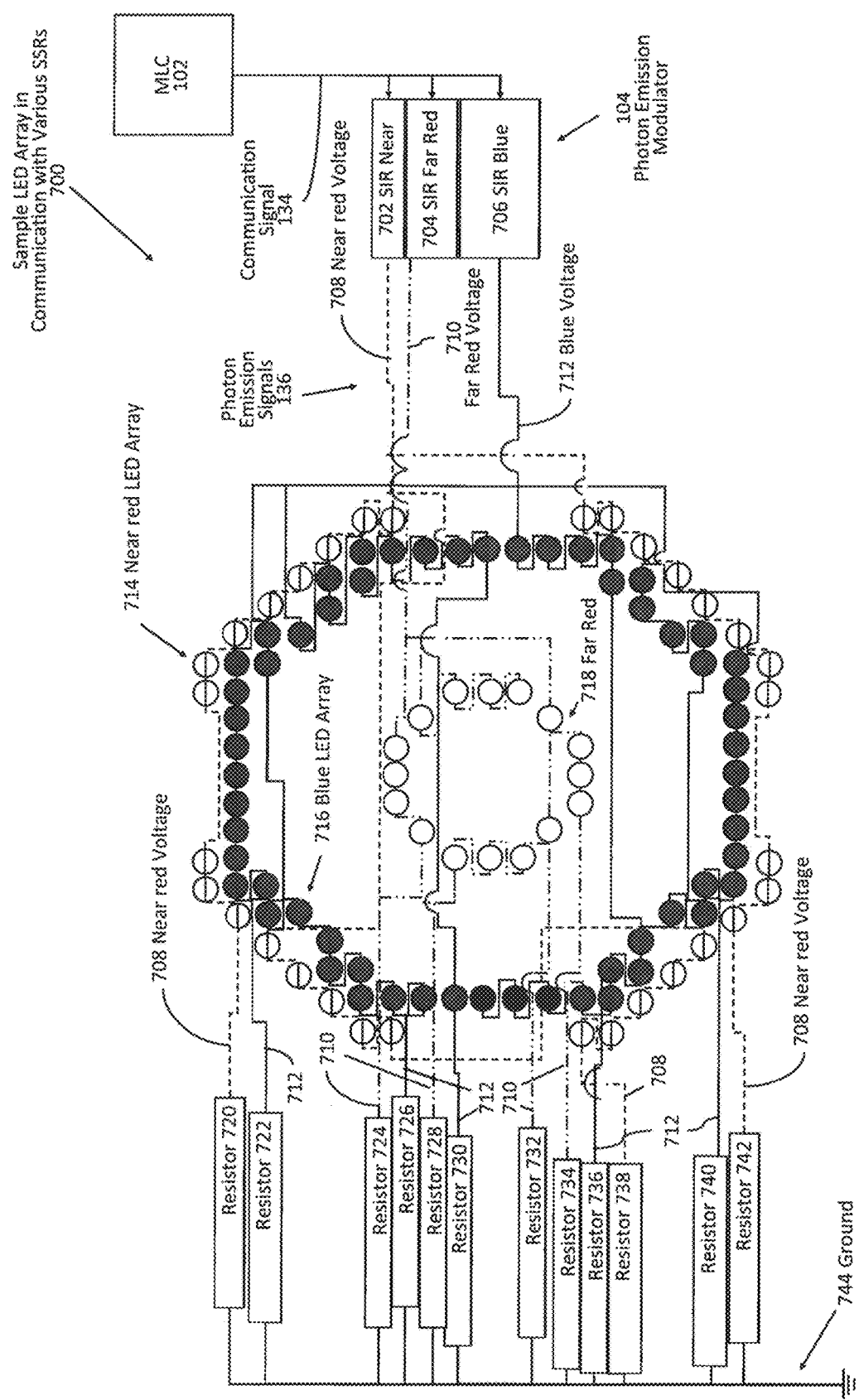
FIG. 7 is a diagram showing a sample LED array in communication with various SSRs (Solid State Relays), BJTs or FETS.

FIG. 7 provides an example of one embodiment of an array of LEDs in communication with a series of solid-state relays or SSRs 700. As shown in FIG. 7 and repeated from FIG. 1, a MLC 102 is in communication by means of a communication signal 134 with a photon emission modulation controller 104. The photon emission modulation controller 104 of this example contains three SSRs. The MLC 102 outputs a signal to control the SSRs. The first SSR controls an array of near-red LEDs 702, the second SSR controls an array of far-red LEDs 704 and the third SSR to controls an array of blue LEDs 706. Each SSR 702, 704 and 706 is in communication with an array of LEDs, 714, 716 and 718 by means of a photon emission signal 136. As shown in FIG. 7, the near-red SSR 702 sends a photon emission signal 136 to initiate a photon pulse of the near-red LEDS 714 comprising a near-red voltage 708 to an array of near-red LEDs 714. The near-red voltage 708 is then transmitted from the array of near-red LEDs 714 to a series of resistors 720, 742, 738, such as a 68-ohm resistor, with each resistor 720, 742 and 738 connected to a ground 744.

As further shown in FIG. 7, the far-red SSR 704 sends a photon emission signal 136 to initiate a photon pulse of far-red LEDs comprising a far-red voltage 710 to an array of red LEDs 718. The red voltage 710 is then transmitted from the red LED array 718 and a series of resistors 724, 728, 732 and 734, such as 390-ohm resistor with each resistor 724, 728, 732 and 734 connected to a ground 744. FIG. 7 also shows the blue SSR 706 sending a photon emission signal 136 to initiate a photon pulse of blue LEDs comprising a blue voltage 712 to an array of blue LEDs 716. The blue voltage 712 is then transmitted from the array of blue LEDs 716 and transmitted to a series of resistors 722, 726, 730, 736 and 740, such as a 150-ohm resistor, with each resistor 722, 726, 730, 736 and 740 connected to a ground 744.

Figure 8B:
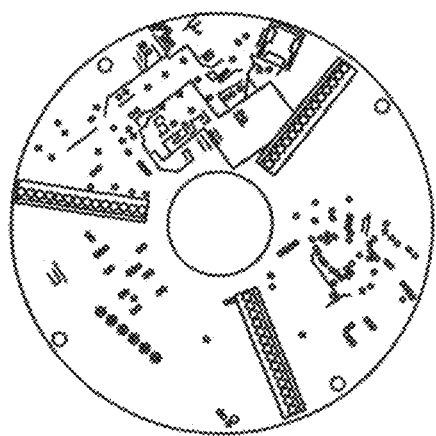
Figure 8D:
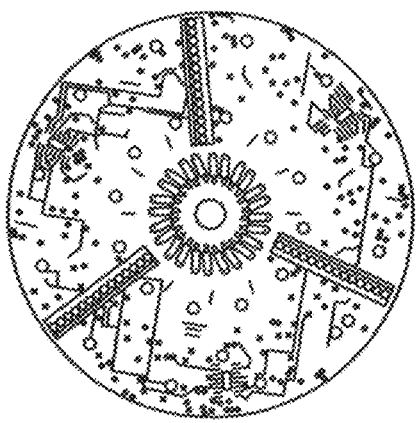
FIG. 8d is a photo showing the backside of the LED array of FIG. 8c with a replaceable multicolor die LED.
Figure 8A:
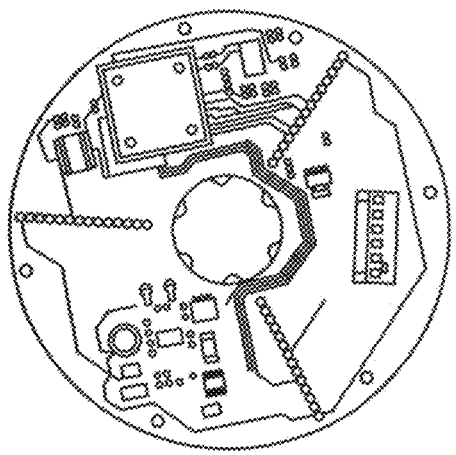
FIG. 8a is a photo showing the power converter, SPI, and microcontroller of a multiple colored die within a single LED.
Figure 8C:
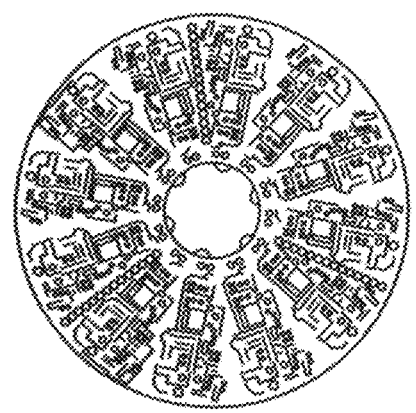

FIGS. 8*a* to 8*d* show various aspects of an example light assembly for the emission of photons within a signal for use in systems and methods described herein. FIG. 8*a* is a photo showing a power converter, serial peripheral interface (SPI), and microcontroller of a multiple colored die within a light assembly. FIG. 8*b* is a photo showing the backside of the multiple colored die within the light assembly of FIG. 8*a*. FIG. 8*c* is a photo showing the high-speed switching circuitry for flashing of the multiple colored die within the light assembly of FIG. 8*a*. FIG. 8*d* is a photo showing the backside of the light assembly of FIG. 8*c* with a replaceable multicolor die LED.

Figure 9:
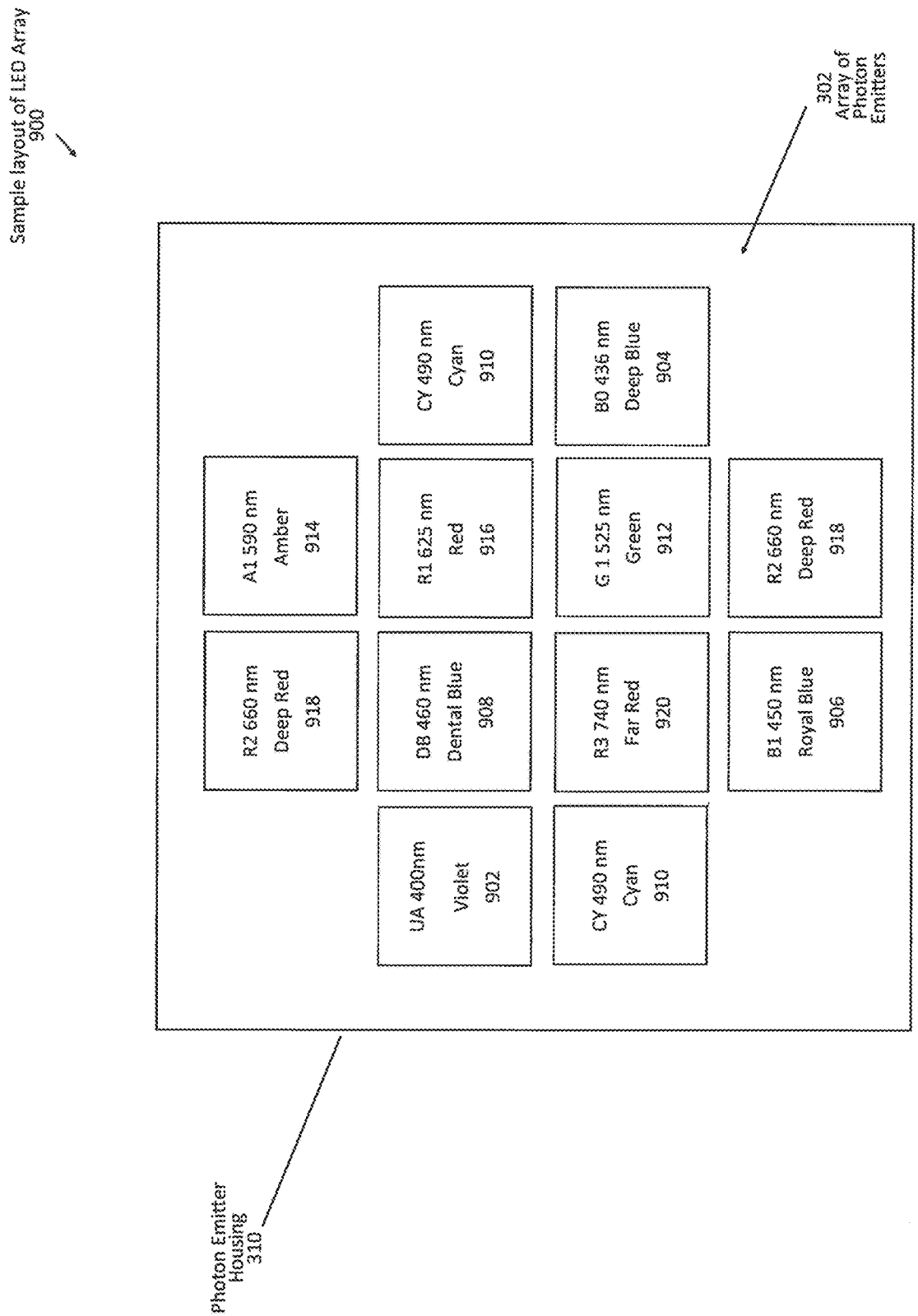
FIG. 9 is an example layout of LEDs within a LED array.

The light assembly of FIGS. 8*a* to 8*d* may be used in several embodiments described herein, including a master/slave system, where a master photon emitter contains all logic and controls for the emission of photons and signals from the master photon emitter as well as any additional photon emitters in communication with the master photon emitter. The light assembly of FIGS. 8*a*-8*d* may also be used in a controller system. As discussed above, controller is in communication with two or more photon emitters FIG. 9 provides an example layout of LEDs within a LED array 900. As shown in FIG. 9, twelve LEDs form an array of photon emitters 302 in a photon emitter housing 310. The sample layout includes 400 nm (violet) 902, 436 nm (deep blue) 904, 450 nm (royal blue) 906, 460 nm (dental blue) 908, 490 nm (cyan) 910, 525 nm (green) 912, 590 nm (amber) 914, 625 nm (red) 916, 660 nm (deep red) 918, and 740 nm (far red) 920.

Figure 10:
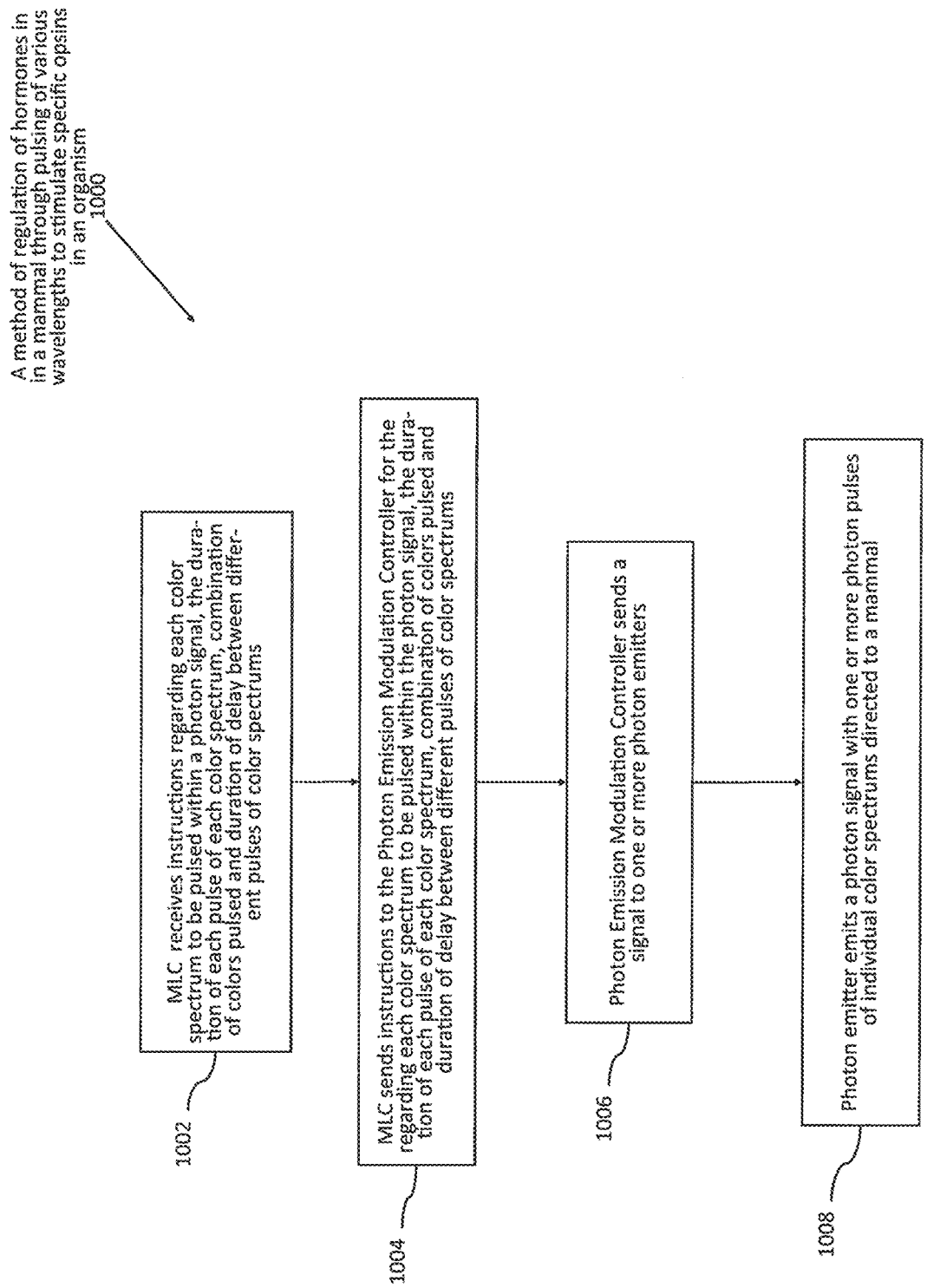
FIG. 10 is a flow diagram showing a method of regulation of hormones in a mammal through pulsing of various wavelengths to stimulate specific opsins in an organism.

FIG. 10 is a flow diagram showing the method of modulation of individual color spectrums pulsed for mammal hormone production 1000. As shown in FIG. 10, in step 1002, the master logic controller receives instructions regarding each individual color spectrum to be pulsed within in a signal, the duration of each pulse of each color spectrum within a signal, the combination of colors to be pulsed and duration of delay between each color spectrum pulse. Instructions and information sent to the master logic controller may relate to the photon pulse duration of each color to be pulsed, photon pulse delay, intensity, frequency, duty cycle, mammal type, state of maturity of the mammal and the type of hormone to be produced. In step 1004, the master logic controller sends instructions to the photon emission modulation controller the regarding each color spectrum to be pulsed, the duration of each pulse of each color spectrum, combination of colors pulse and duration of delay between different color spectrums. In step 1006, the photon emission modulation controller sends at least one signal to one or more photon emitters capable of emitting pulses of one or more individual color spectrums toward a mammal, such as green LEDs, far-red LEDs, blue LEDs and orange LEDs. In step 1008, one or more photon emitters emit one or more photon pulses of individual color spectrums directed to a mammal allowing for specific opsins within the mammal to be stimulated to regulate hormone production. The methods for regulation of hormone production allow for hormones in a mammal to in in production levels by 0.1%, 1.0%, 5%, 7.5, 10%, 12.2%, 20%, 33.3%, 50%, 81.7%, 100%, 143.9%, 150%, 181.4%, 200%, 250%, 444.2%, 500% and 1000% and all integers in between, over the baseline hormone level of a mammal. Conversely, the methods described herein also allow for the production of hormone levels to decrease from 0.1%, 1.2%, 7.7%, 10%, 15.6, 20%, 47.2%, 50%, 74.5%, 100%, 150%, 200%, 250%, 500% and 1000% and all integers in between, under the baseline hormone level of a mammal as in the mammal, as will be understood by one skilled in the art, once they understand the disclosure provided herein.

Figure 11:
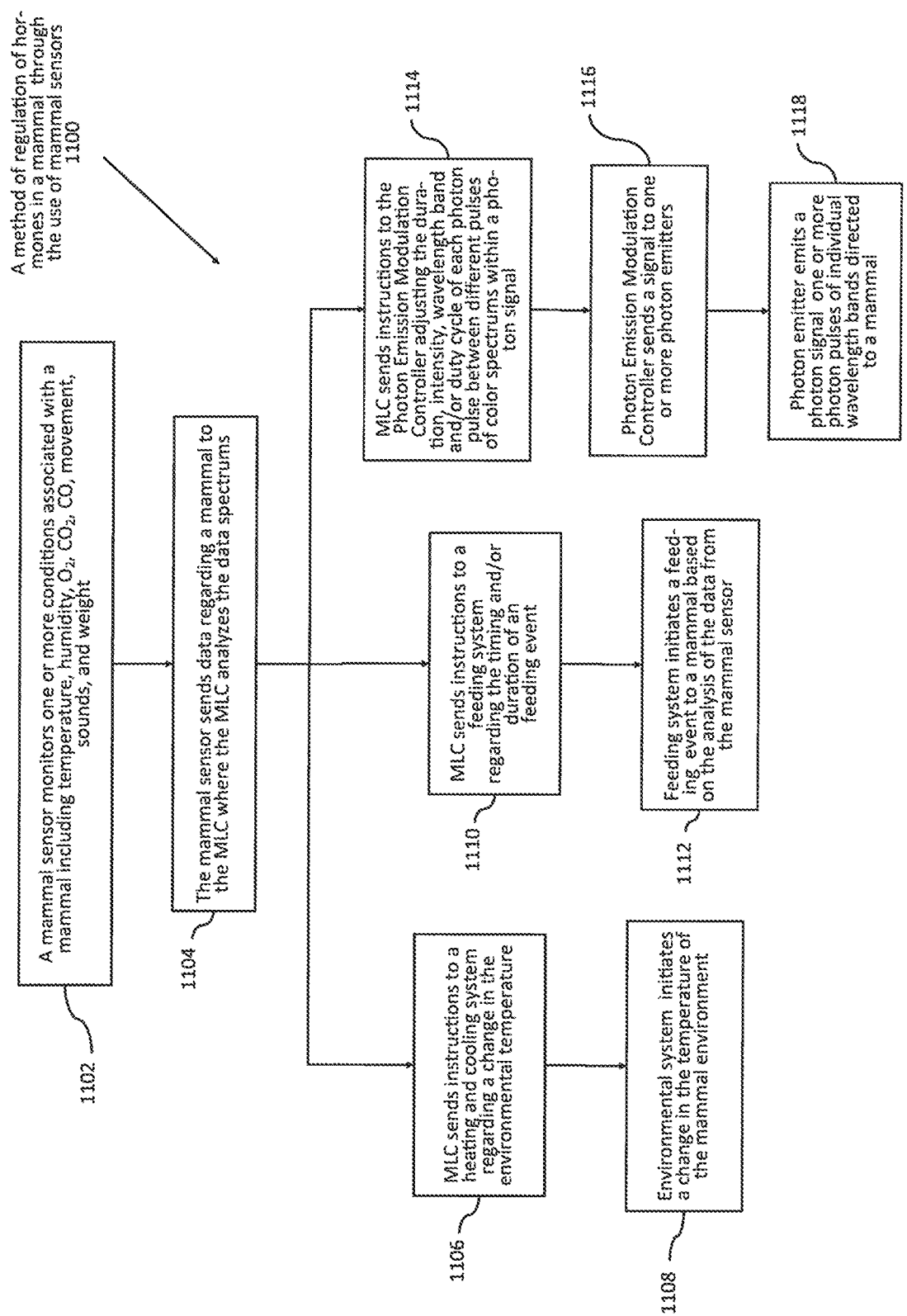
FIG. 11 is a flow diagram showing a method of regulation of hormones, behavior, reproduction cycling, hair growth, calming or metabolism rates. in a mammal through the use of mammal sensors.

FIG. 11 provides an additional embodiment of the present disclosure, showing a flowing diagram of the regulation of hormones in a mammal based on information from mammal sensors 1100. As shown in step 1102, a mammal sensor monitors one or more conditions associated with the environment of a mammal. The conditions to be monitored by include but is not limited to the air temperature, humidity, the mammal's body temperature, weight, sound, movement of the mammal, infrared, $O_2$, $CO_2$ and CO. In step 1104, the mammal sensor sends data regarding the environmental or physical conditions associated with a mammal to the MLC. The MLC then analyzes the data sent from the mammal sensor or the analysis may be done by a third-party software program that is remote to the system. In step 1106, based on the information from the mammal sensor, the MLC sends instructions to change an embodiment of the environment such as air temperature or humidity. In step 1108, the environmental system initiates an event to one or more animals based on the analysis of the data from the sensor. As will be understood by one skilled in the art, the adjustment of the event can be on a micro level, such as an adjustment to the environment of one specific mammal or the adjustment can be on a macro level such as an entire growth chamber or operation. In step 1110, based on the information from the mammal sensor the MLC sends instructions to a feeding system, nutrient system or nutrient source, such as a drip, nutrient film or nutrient injection system, regarding the timing and/or concentration of the nutrient to be distributed to a mammal during a nutrient event. In step 1112, nutrient system initiates a nutrient event where nutrients are directed to a mammal based on the analysis of the data from the mammal sensor. As will be understood by one skilled in the art, the adjustment of the nutrient event can be on a micro level, such as an adjustment to the nutrients to one specific mammal or the adjustment can be on a macro level such as an entire growth chamber or operation. In step 1114, based on the analysis of the data from the mammal sensor, the MLC sends instructions to the photon emission modulation controller adjusting the duration, intensity, color spectrum and/or duty cycle of each photon pulse between different pulses of color spectrums to a specific an animal or to a group of animals. In step 1116, the photon emission modulation controller sends a signal to one or more photon emitters adjusting the duration, intensity, color spectrum and/or duty cycle of each photon pulse between different pulses of color spectrums to a specific an animal or to a group of animals. In step 1118, based on the signal received from the photon emission modulation controller, one or more photon emitters emit one or more photon pulses of individual color spectrums directed to an animal or to a group of animals.

Figure 12:
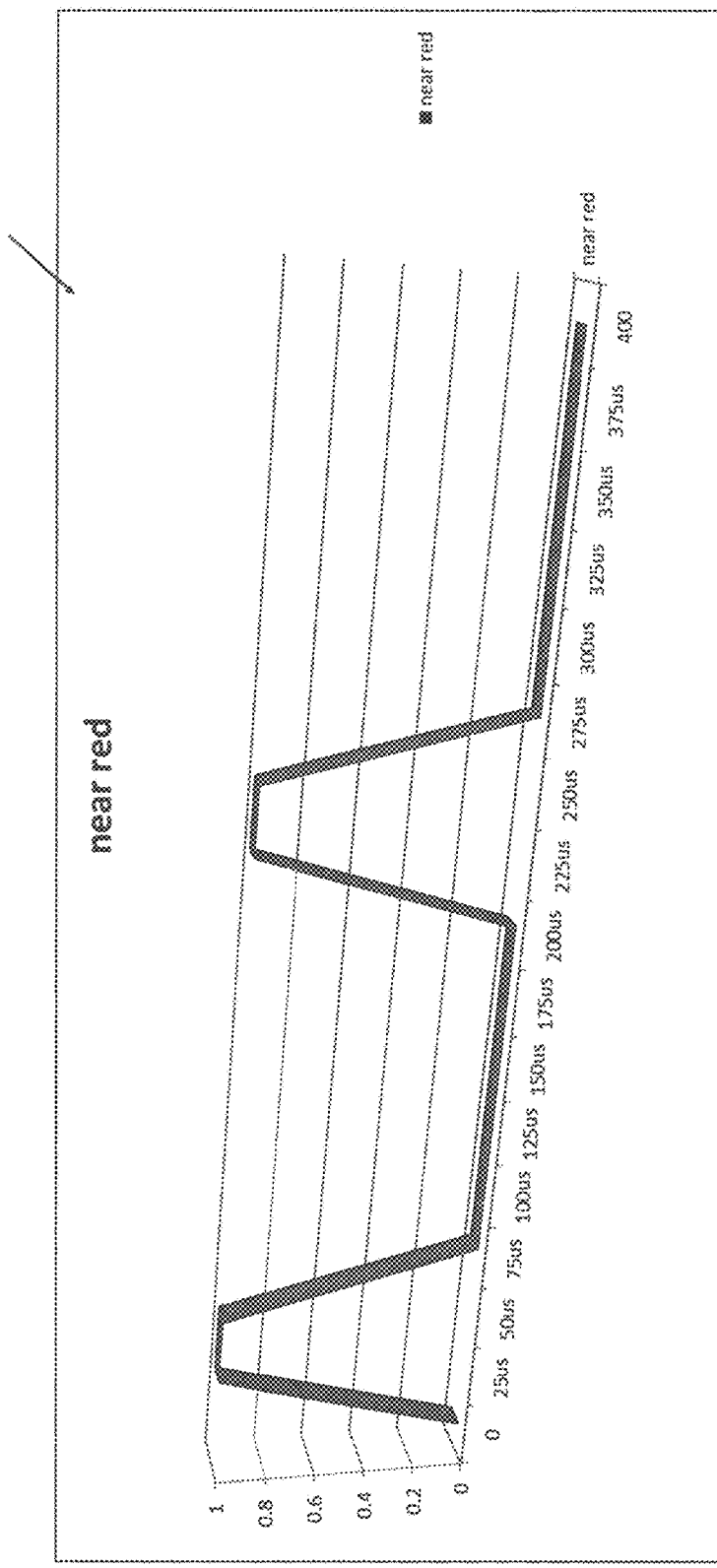
FIG. 12 is a graph showing an example of a photon signal with a photon pulse of near red, with the photon signal having a repetitive rate of 400 μs for the regulation of hormone production in mammals.

FIG. 12 is a graph showing an example photon signal with a repetitive photon pulse of near-red, showing a duration ON and a duration OFF for the controlled regulation of hormones in mammals. As shown in FIG. 12 and previously described in FIGS. 1-11, an example of the cycling of a photon signal with repetitive photon pulses of one color spectrums within the photon signal is provided where a photon signal having a repetitive near-red photon pulse is emitted from a photon emitter. As shown in the graph near-red spectrum is pulsed first followed by a delay. Next, a second pulse comprising of near-red spectrum is again pulsed followed by a delay. This photon signal may be repeated indefinitely or until the mammal hormone production under and receiving the photon pulses has reached its desired production amount. While in this descriptive example of a photon signal having a repetitive photon pulse set comprising offset pulsing of one color spectrum, it should be understood that this description is applicable to any such system with other emissions of photon pulses over a period of time, as various combinations of pulses of color spectrums including but not limited to near-red, far-red, infra-red, green blue, yellow, orange and ultraviolet excluding the standard analog frequency lighting emission standards of the United States of 60 Hz and Europe of 50 Hz. Examples of the photon pulse duration between pulses of each individual color spectrum or color spectrum combinations may include but is not limited to, 0.01 microseconds to 5000 milliseconds and all integers in between. The system of the present disclosure also allows for other durations between pulses of each individual color spectrum or color spectrum combinations including but not limited to 0.1 microsecond to 24 hours, and all integers in between. The system of the present disclosure may be programmed to allow for variations of photon emission as well as variations of photon emission delay to allow for events such as extended dark cycles.

Figure 13:
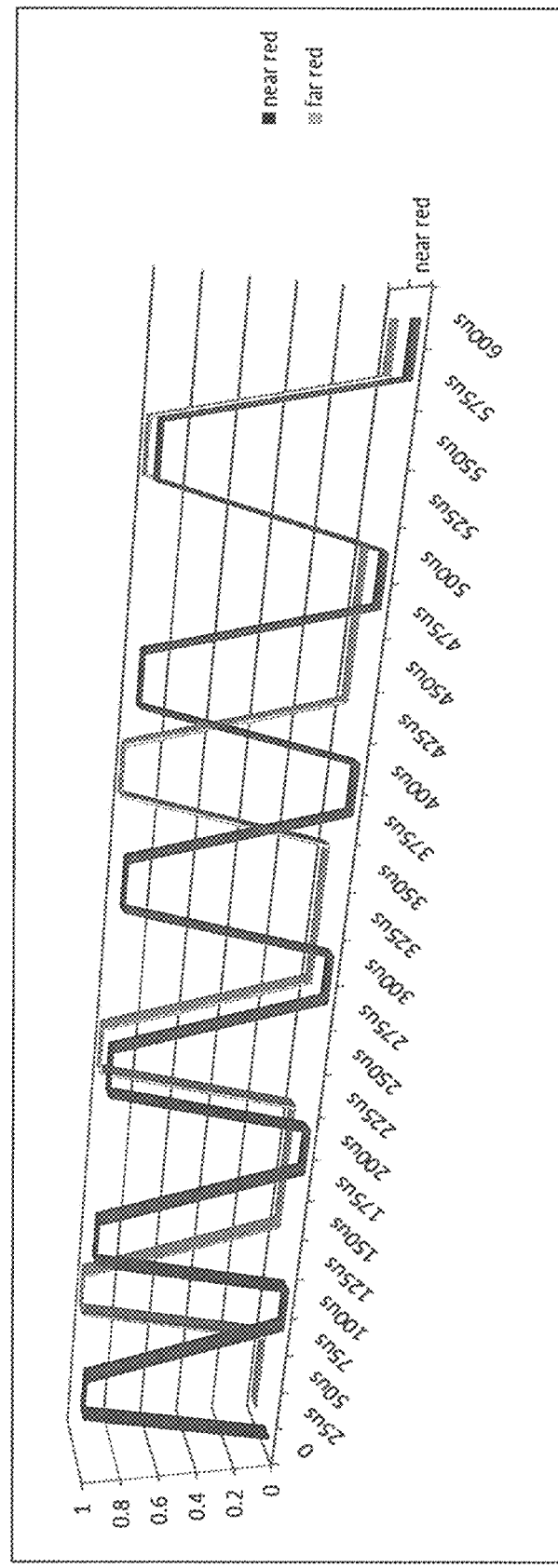
FIG. 13 is a graph showing an example of a photon signal with a photon pulse of near red and a photon pulse of far red, with the photon signal having a repetitive rate of 600 μs for the regulation of hormone production in mammals.

FIG. 13 is a graph showing an example photon signal containing photon pulses of two color spectrums, near-red and far red. The time scale on this chart is not to scale but serves as an example embodiment exhibiting the variation of color spectrum, duration ON, duration OFF frequency and duty cycle within a photon signal that may be utilized to regulation hormone production. As shown in FIG. 13 and previously described in FIGS. 1-11, another example of a signal producing simultaneously and cycling photon pulses of various color spectrum of the present disclosure is provided where photon signal comprising photon pulses of two color spectrums are emitted from a photon emitter. As shown in the graph a signal provides a far-red spectrum that is pulsed first followed by a delay and then a pulse of a near-red spectrum and then followed by a delay. Next, a second pulse of near red is initiated followed by a delay followed by an individual pulse of far-red. This photon signal may be repeated indefinitely or until the desired mammal response has been initiated under and receiving the photon pulses. As discussed above, this example may also be used to stimulate hormones for ovulation or to reset the mammal's circadian rhythm. While in this descriptive example of a photon pulse set comprising offset pulsing of two color spectrum, it should be understood that this description is applicable to any such system with other emissions of photon pulses over a period of time, as various combinations of pulses of color spectrums including but not limited to near-red, far-red, infra-red, green, blue, yellow, orange and ultraviolet excluding the standard analog frequency lighting emission standards of the United States of 60 Hz and Europe of 50 Hz. Examples of the photon pulse duration between pulses of each individual color spectrum or color spectrum combinations may include but is not limited to, 0.01 microseconds to 5000 milliseconds and all integers in between. The system of the present disclosure also allows for other durations between pulses of each individual color spectrum or color spectrum combinations including but not limited to 0.1 microsecond to 24 hours, and all integers in between. The system of the present disclosure may be programmed to allow for variations of photon emission as well as variations of photon emission delay to allow for events such as extended dark cycles.

Figure 14:
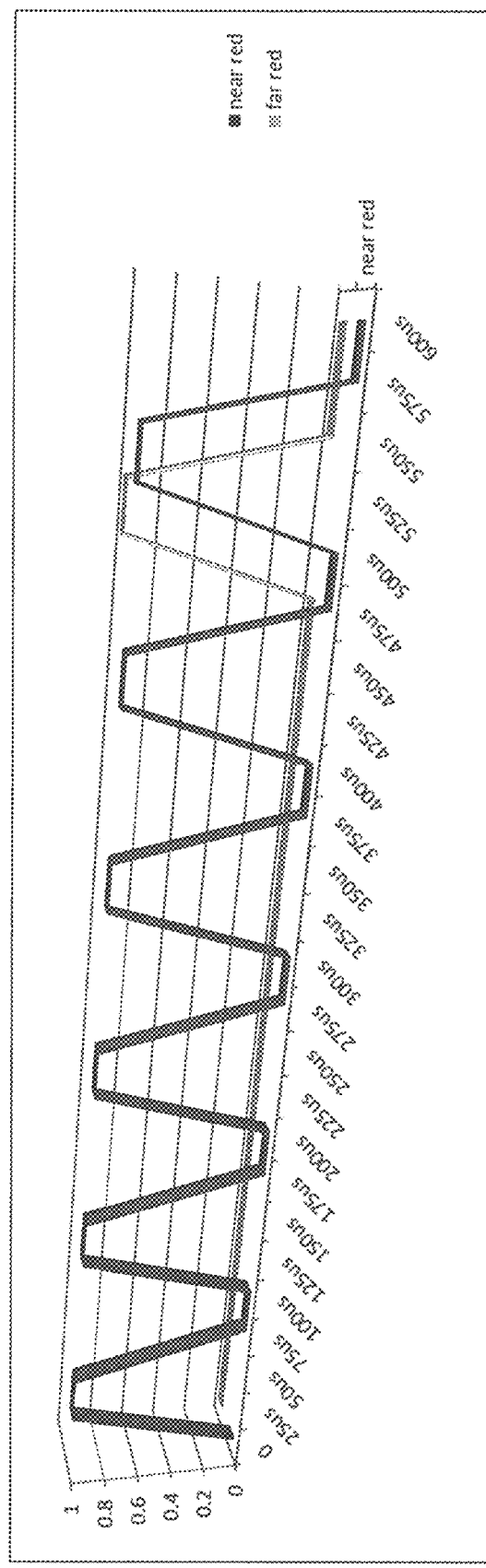
FIG. 14 is a second graph showing an example of a photon signal with a photon pulse of near red and a photon pulse of far red, where the two photon pulses have a different duration ON and duration OFF from the example shown in FIG. 13, with the photon signal having a repetitive rate of 600 μs for the regulation of hormone production in mammals.

FIG. 14 is a graph showing a second example photon signal containing photon pulses of two color spectrums, near-red and far red. Again, the time scale on this chart is not to scale but serves as an example embodiment exhibiting the variation of color spectrum, duration ON, duration OFF frequency and duty cycle within a photon signal that may be utilized to regulate hormone production. As shown in FIG. 14 and previously described in FIGS. 1-11, another example of the cycling of photon pulses of various color spectrum of the present disclosure is provided where photon signal comprising photon pulses of two color spectrums are emitted from a photon emitter. As shown in the graph, a far-red spectrum is pulsed in a series or pulse train of five pulses followed by a pulse of a near-red spectrum and then followed by a delay. This photon signal may be repeated indefinitely or until the desired mammal hormone level has been achieved. As discussed above, this example may also be used to regulation hormone production for the stimulate ovulation or to reset the mammal's circadian rhythm. While in this descriptive example of a photon pulse set comprising offset pulsing of two color spectrum, it should be understood that this description is applicable to any such system with other emissions of photon pulses over a period of time, as various combinations of pulses of color spectrums including but not limited to near-red, far-red, infra-red, green, blue, yellow, orange and ultraviolet excluding the standard analog frequency lighting emission standards of the United States of 60 Hz and Europe of 50 Hz. Examples of the photon pulse duration between pulses of each individual color spectrum or color spectrum combinations may include but is not limited to, 0.01 microseconds to 5000 milliseconds and all integers in between. The system of the present disclosure also allows for other durations between pulses of each individual color spectrum or color spectrum combinations including but not limited to 0.1 microsecond to 24 hours, and all integers in between. The system of the present disclosure may be programmed to allow for variations of photon emission as well as variations of photon emission delay to allow for events such as extended dark cycles.

Figure 15:
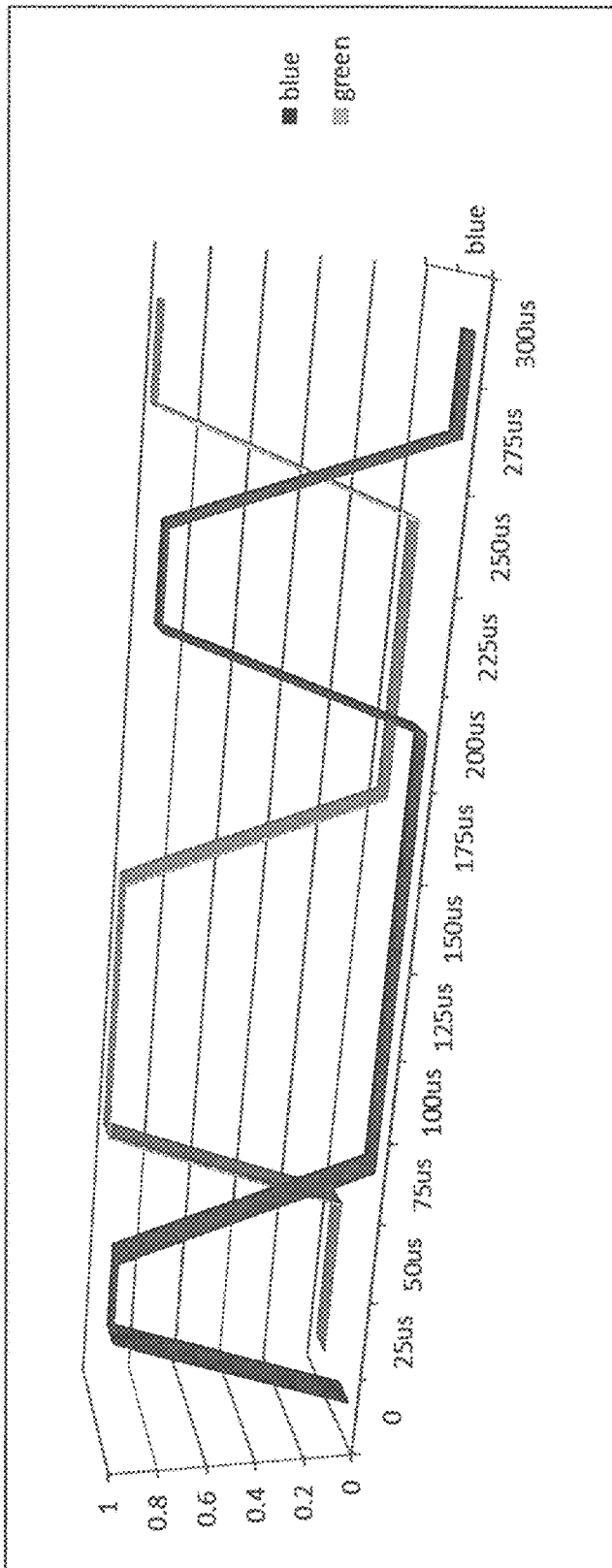
FIG. 15 is a graph showing an example of a photon signal with a photon pulse of blue and a photon pulse of green, with the photon signal having a repetitive rate of 600 μs for the regulation of hormone production in mammals.

FIG. 15 is a graph showing an example photon signal containing photon pulses of two color spectrums, blue and green. The time scale on this chart is not to scale but serves as an example embodiment exhibiting the variation of color spectrum, frequency and duty cycle that may be utilized to stimulate hunger or a specific mood and to reset the circadian rhythm of the mammal. As shown in FIG. 15 and previously described in FIGS. 1-11, another example of the cycling of photon pulses of various color spectrum of the present disclosure is provided where photon pulses of two color spectrums are emitted from a photon emitter. As shown in the graph pulses of blue and green are pulsed first followed by a delay. Next, a second pulse of blue is initiated followed by a delay followed by an individual pulse of green. This cycle may be repeated indefinitely or until the desired mammal response has been initiated under and receiving the photon pulses. As discussed above, this example may also be used to regulate hormones, hunger, mood or even to reset the mammal's circadian rhythm. While in this descriptive example of a photon pulse set comprising offset pulsing of two color spectrum, it should be understood that this description is applicable to any such system with other emissions of photon pulses over a period of time, as various combinations of pulses of color spectrums including but not limited to near-red, far-red, infrared, green, blue, yellow, orange and ultraviolet excluding the standard analog frequency lighting emission standards of the United States of 60 Hz and Europe of 50 Hz. Examples of the photon pulse duration between pulses of each individual color spectrum or color spectrum combinations may include but is not limited to, 0.01 microseconds to 5000 milliseconds and all integers in between. The system of the present disclosure also allows for other durations between pulses of each individual color spectrum or color spectrum combinations including but not limited to 0.1 microsecond to 24 hours, and all integers in between. The system of the present disclosure may be programmed to allow for variations of photon emission as well as variations of photon emission delay to allow for events such as extended dark cycles.

Figure 16:
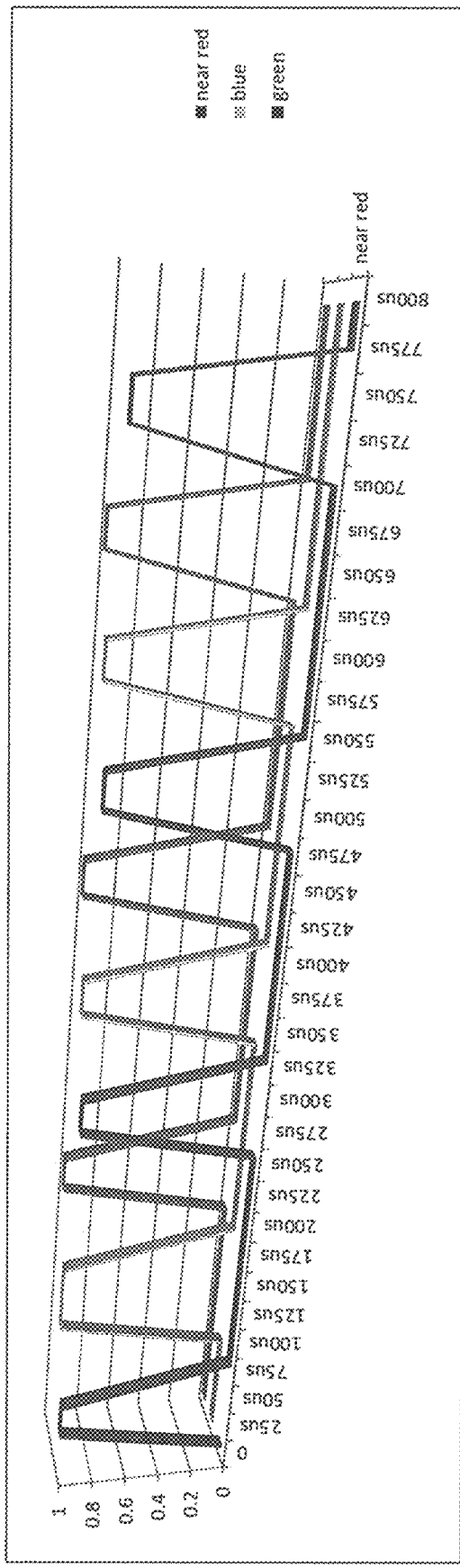
FIG. 16 is a graph showing an example of a photon signal with a photon pulse of blue, a photon pulse of green, and a pulse of near red with the photon signal having a repetitive rate of 800 μs for the regulation of hormone production in mammals.

FIG. 16 graph showing an example photon signal containing photon pulses of three color spectrums, near-red, blue and green. The time scale on this chart is not to scale but serves as an example embodiment exhibiting the variation of color spectrum, frequency and duty cycle that may be utilized to stimulate ovulation, hunger or a specific mood and to reset the circadian rhythm of the mammal. As shown in FIG. 16 and previously described in FIGS. 1-11, another example of the cycling of photon pulses of various color spectrum of the present disclosure is provided where photon pulses of three color spectrums are emitted from a photon emitter. As shown in the graph, a pulse of near red is provided followed by a delay. Next, a pulse of blue is initiated followed by a delay followed by an individual pulse of green. This signal and cycle may be repeated indefinitely or until the desired mammal response has been initiated under and receiving the photon pulses. As discussed above, this example may also be used to regulate hormones, ovulation, hunger, mood or even to reset the mammal's circadian rhythm. While in this descriptive example of a photon pulse set comprising offset pulsing of three color spectrums, it should be understood that this description is applicable to any such system with other emissions of photon pulses over a period of time, as various combinations of pulses of color spectrums including but not limited to near-red, far-red, infra-red, green, blue, yellow, orange and ultraviolet excluding the standard analog frequency lighting emission standards of the United States of 60 Hz and Europe of 50 Hz. Examples of the photon pulse duration between pulses of each individual color spectrum or color spectrum combinations may include but is not limited to, 0.01 microseconds to 5000 milliseconds and all integers in between. The system of the present disclosure also allows for other durations between pulses of each individual color spectrum or color spectrum combinations including but not limited to 0.1 microsecond to 24 hours, and all integers in between. The system of the present disclosure may be programmed to allow for variations of photon emission as well as variations of photon emission delay to allow for events such as extended dark cycles.

Figure 17:
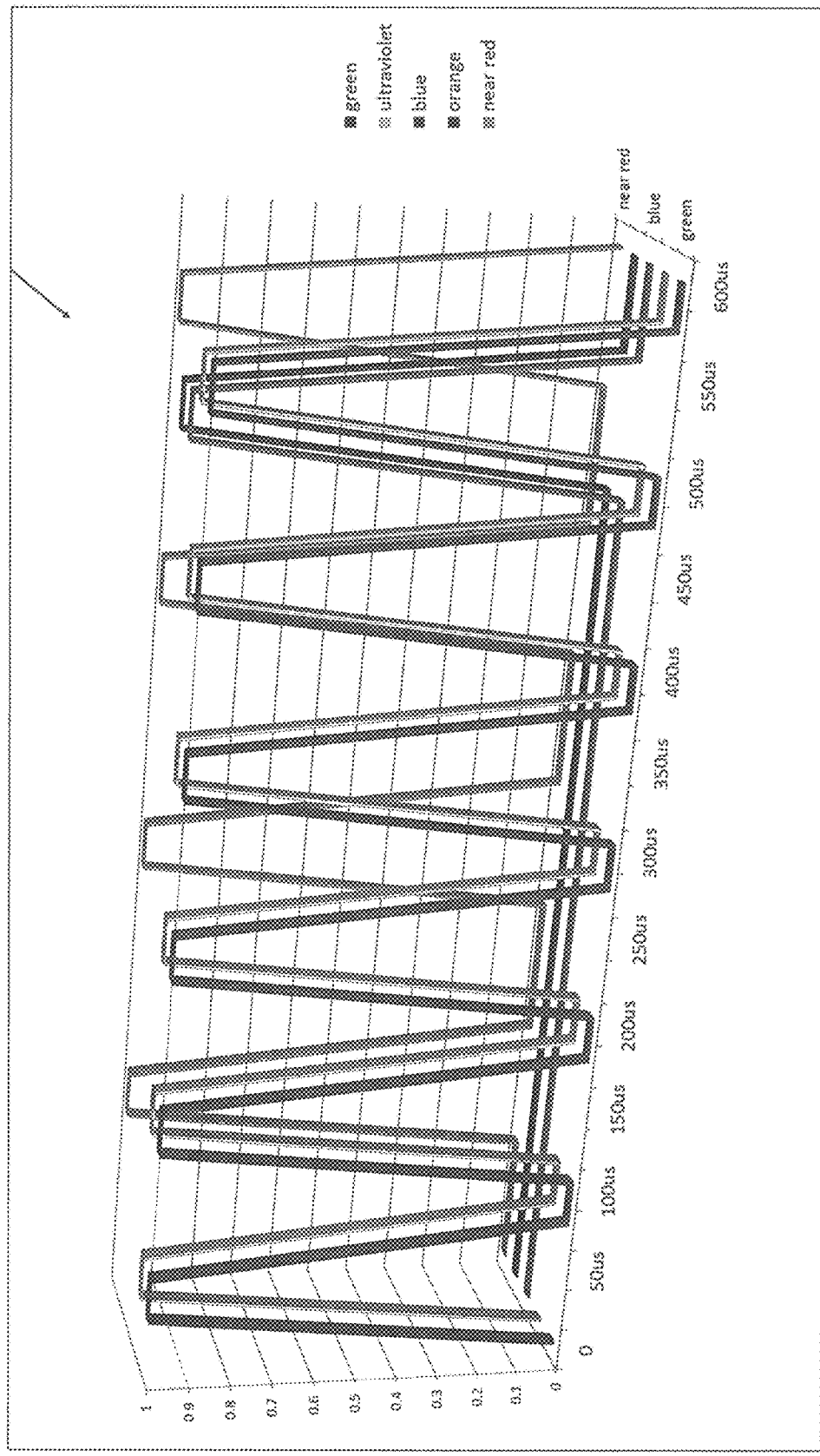
FIG. 17 is a graph showing an example of a photon signal with a photon pulse of blue, a photon pulse of ultraviolet, a photon pulse of orange, a photon pulse of green, and a pulse of near red with the photon signal having a repetitive rate of 600 μs for the regulation of hormone production in mammals.

FIG. 17 graph showing an example photon signal containing photon pulses of five color spectrums, green, ultraviolet, orange, near-red, and blue. The time scale on this chart is not to scale but serves as an example embodiment exhibiting the variation of color spectrum, frequency and duty cycle that may be utilized to regulate hormones, ovulation, hunger or a specific mood and to reset the circadian rhythm of the mammal. As shown in FIG. 17 and previously described in FIGS. 1-11, another example of the cycling of photon pulses of various color spectrum of the present disclosure is provided where photon pulses of five color spectrums are emitted from a photon emitter. As shown in the graph, pulses of green and ultraviolet are provided followed by a delay. Next, a pulse of near red is initiated followed by a delay followed pulses of green and ultraviolet. This cycle may be repeated with five pulses of green and ultraviolet and three pulses of near red and then a single pulse of blue and orange. This pulse signal may be repeated indefinitely or until the desired mammal response has been initiated under and receiving the photon pulses. As discussed above, this example may also be used to regulate hormones, ovulation, hunger, mood or even to reset the mammal's circadian rhythm. While in this descriptive example of a photon pulse set comprising offset pulsing of three color spectrums, it should be understood that this description is applicable to any such system with other emissions of photon pulses over a period of time, as various combinations of pulses of color spectrums including but not limited to near-red, far-red, infra-red, green, blue, yellow, orange and ultraviolet excluding the standard analog frequency lighting emission standards of the United States of 60 Hz and Europe of 50 Hz. Examples of the photon pulse duration between pulses of each individual color spectrum or color spectrum combinations may include but is not limited to, 0.01 microseconds to 5000 milliseconds and all integers in between. The system of the present disclosure also allows for other durations between pulses of each individual color spectrum or color spectrum combinations including but not limited to 0.1 microsecond to 24 hours, and all integers in between. The system of the present disclosure may be programmed to allow for variations of photon emission as well as variations of photon emission delay to allow for events such as extended dark cycles.

Figure 18:
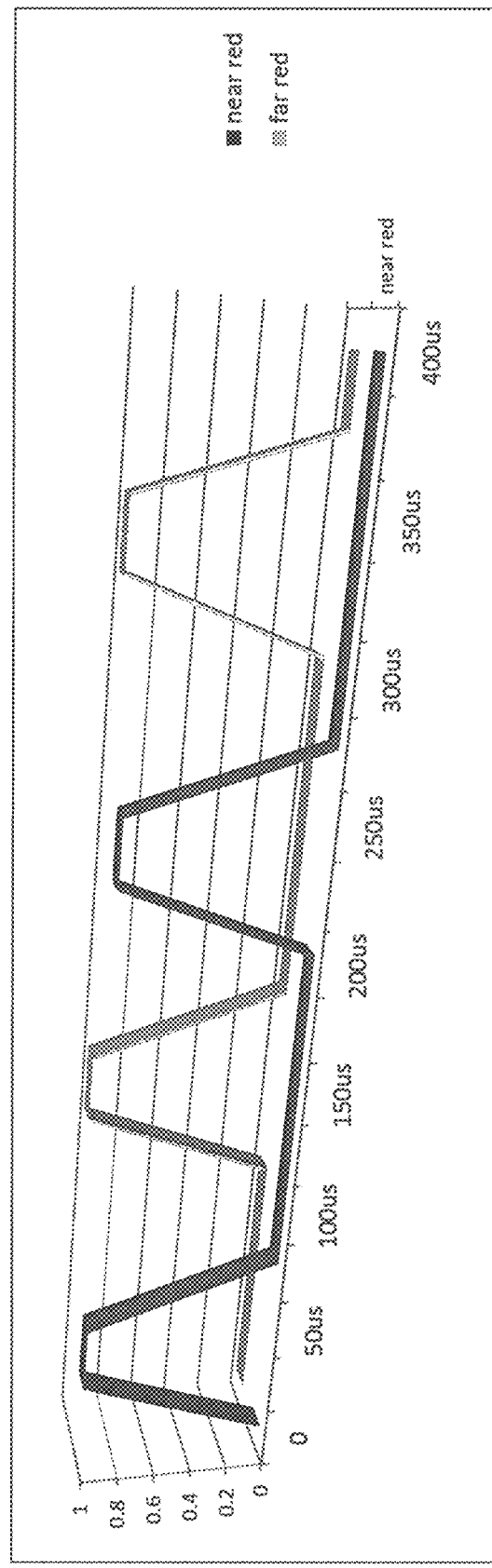
FIG. 18 is a third graph showing an example of a photon signal with a photon pulse of near red and a photon pulse of far red, where the two photon pulses have a different duration ON and duration OFF from the examples shown in FIG. 13 and FIG. 14, with the photon signal having a repetitive rate of 400 μs for the regulation of hormone production in mammals.

FIG. 18 is a graph showing a third example photon signal containing photon pulses of two color spectrums, near-red and far red. The time scale on this chart is not to scale but serves as an example embodiment exhibiting the variation of color spectrum, duration ON, duration OFF frequency and duty cycle within a photon signal that may be utilized to regulate hormones. As shown in FIG. 18 and previously described in FIGS. 1-11, another example of the cycling of photon pulses of various color spectrum of the present disclosure is provided where photon signal comprising photon pulses of two color spectrums are emitted from a photon emitter. As shown in the graph a far-red spectrum is pulsed first followed by a delay and then a pulse of a near-red spectrum and then followed by a delay. Next, a second pulse of near red is initiated followed by a delay followed by an individual pulse of far-red. This photon signal may be repeated indefinitely or until the desired mammal response has been initiated under and receiving the photon pulses. As discussed above, this example may also be used to regulate hormone, ovulation or to reset the mammal's circadian rhythm. While in this descriptive example of a photon pulse set comprising offset pulsing of two color spectrum, it should be understood that this description is applicable to any such system with other emissions of photon pulses over a period of time, as various combinations of pulses of color spectrums including but not limited to near-red, far-red, infra-red, green, blue, yellow, orange and ultraviolet excluding the standard analog frequency lighting emission standards of the United States of 60 Hz and Europe of 50 Hz. Examples of the photon pulse duration between pulses of each individual color spectrum or color spectrum combinations may include but is not limited to, 0.01 microseconds to 5000 milliseconds and all integers in between. The system of the present disclosure also allows for other durations between pulses of each individual color spectrum or color spectrum combinations including but not limited to 0.1 microsecond to 24 hours, and all integers in between. The system of the present disclosure may be programmed to allow for variations of photon emission as well as variations of photon emission delay to allow for events such as extended dark cycles.

Figure 19:
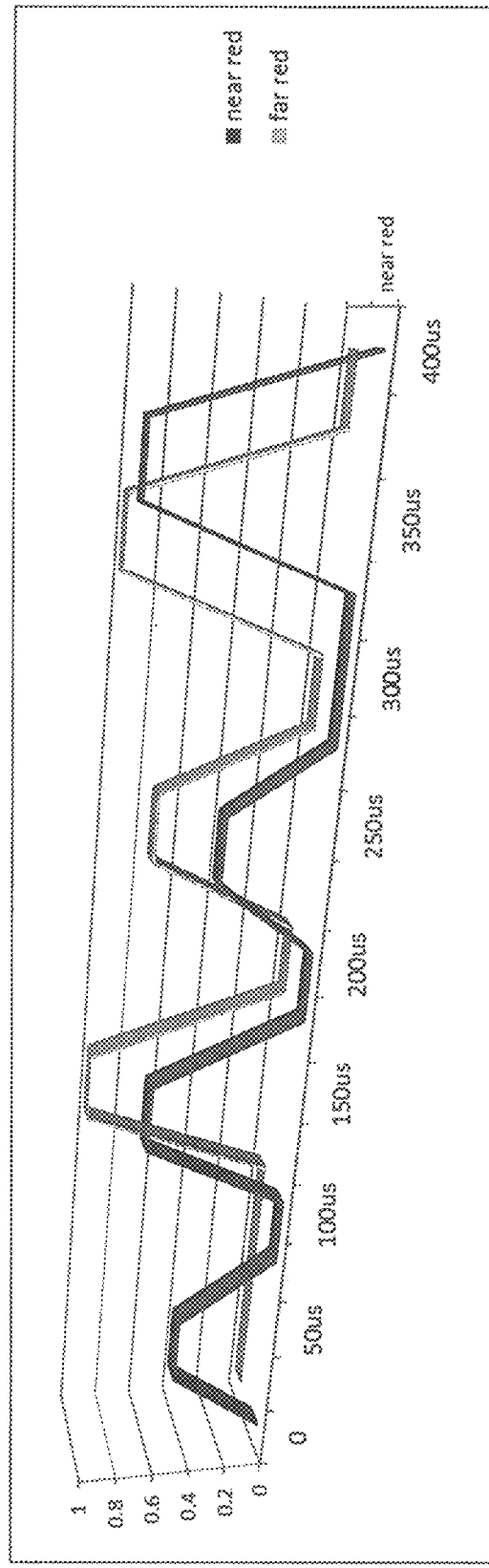
FIG. 19 is a fourth graph showing an example of a photon signal with a photon pulse of near red and a photon pulse of far red, where the two photon pulses have a different duration ON with different intensities and duration OFF from the examples shown in FIG. 13 and FIG. 14, with the photon signal having a repetitive rate of 400 μs for the regulation of hormone production in mammals.

FIG. 19 is a graph showing an example photon signal containing photon pulses of two color spectrums, near-red and far red. The time scale on this chart is not to scale but serves as an example embodiment exhibiting the variation of color spectrum, duration ON with varying intensities, duration OFF frequency and duty cycle within a photon signal that may be utilized to regulate hormones. As shown in FIG. 19 and previously described in FIGS. 1-11, another example of the cycling of photon pulses of various color spectrum of the present disclosure is provided where photon signal comprising photon pulses of two color spectrums are emitted from a photon emitter. As shown in the graph a far-red spectrum is pulsed first followed by a delay and then a pulse of a near-red spectrum and then followed by a delay. Next, a second pulse of near red is initiated followed by a delay followed by an individual pulse of far-red. This photon signal may be repeated indefinitely or until the desired mammal response has been initiated under and receiving the photon pulses. As discussed above, this example may also be used to stimulate ovulation or to reset the mammal's circadian rhythm. While in this descriptive example of a photon pulse set comprising offset pulsing of two color spectrums with varying intensities, it should be understood that this description is applicable to any such system with other emissions of photon pulses over a period of time, as various combinations of pulses of color spectrums including but not limited to near-red, far-red, infra-red, green, blue, yellow, orange and ultraviolet excluding the standard analog frequency lighting emission standards of the United States of 60 Hz and Europe of 50 Hz. Examples of the photon pulse duration between pulses of each individual color spectrum or color spectrum combinations may include but is not limited to, 0.01 microseconds to 5000 milliseconds and all integers in between. The system of the present disclosure also allows for other durations between pulses of each individual color spectrum or color spectrum combinations including but not limited to 0.1 microsecond to 24 hours, and all integers in between. The system of the present disclosure may be programmed to allow for variations of photon emission as well as variations of photon emission delay to allow for events such as extended dark cycles.

Table 4 below provides a table of lighting options. As shown in Table 4, column one provided the name or designation of the lighting option or pulse signal, column two provide the colors pulses in the lighting option, column three is the duration ON of each pulse within the pulse signal, column four is the duration OFF of each pulse within the pulse signal, column five provides the time from ON to OFF.

TABLE 4

| Lighting Option | Colors | Duration ON | Duration OFF | Timing from t-0 | Ma of each color |
|---|---|---|---|---|---|
| Option 1 | Near red 1 | 50 us | 200 us | ON - 0 | 600 |
|  | Near red 2 |  |  | OFF- 50 US |  |
| Option 2 | Near red 1 | 50 us | 50 us | ON - 0 | 600 |
|  | Near red 2 |  |  | OFF- 50 US |  |
|  | Far Red | 50 us | 100 us | ON - 100 us | 900 |
|  |  |  |  | OFF- 150 US |  |
| Option 3 | Near red 1 | 50 us | 100 us | ON - 0 | 600 |

TABLE 4-continued

| Lighting Option | Colors | Duration ON | Duration OFF | Timing from t-0 | Ma of each color |
|---|---|---|---|---|---|
|  | Near red 2 |  |  | OFF- 50 US |  |
|  | Far Red | 50 us | 100 us | ON - 100 us | 900 |
|  |  |  |  | OFF- 150 us |  |
| Option 4 | Near red 1 | 50 us | 200 us | ON - 0 | 600 |
|  | Near red 2 |  |  | OFF- 50 US |  |
| Option 5 | Near red 1 | 50 us | 100 us | ON - 0 | 600 |
|  | Near red 2 |  |  | OFF- 50 US |  |
|  | Far Red | 50 us | 500 us | ON - 150 us | 900 |
|  |  |  |  | OFF- 200 us |  |
| Option 6 | Near red 1 | 50 us | 50 us | ON - 0 | 600 |
|  | Near red 2 |  |  | OFF- 50 US |  |
|  | Far Red | 50 us | 100 us | ON - 100 us | 900 |
|  |  |  |  | OFF - 150 us |  |
| Option 7 | Green | 50 us | 50 us | ON - 0 | 600 |
|  |  |  |  | OFF- 50 US |  |
|  | Far Red | 50 us | 100 us | ON - 100 us | 900 |
|  |  |  |  | OFF- 150 us |  |
| Option 8 | Blue | 50 us | 50 us | ON - 0 | 600 |
|  |  |  |  | OFF- 50 US |  |
|  | Far Red | 50 us | 100 us | ON - 100 us | 900 |
|  |  |  |  | OFF- 150 us |  |
| Option 9 | Near red 1 | 50 us | 100 us | ON - 0 | 600 |
|  | Near red 2 |  |  | OFF- 50 US |  |
|  | Green | 50 us | 500 us | ON - 150 us | 600 |
|  |  |  |  | OFF- 200 us |  |
| Option 10 | Near red 1 | 50 us | 100 us | ON - 0 | 600 |
|  | Near red 2 |  |  | OFF- 50 US |  |
|  | Blue | 50 us | 500 us | ON - 150 us | 600 |
|  |  |  |  | OFF- 200 us |  |
| Option 11 | Near red 1 | 50 us | 100 us | ON - 0 | 600 |
|  |  |  |  | OFF- 50 US |  |
|  | Blue | 50 us | 500 us | ON - 150 us | 600 |
|  |  |  |  | OFF- 50 US |  |
|  | Green | 50 us | 50 us | ON - 0 | 600 |
|  |  |  |  | OFF- 50 US |  |
| Option 12 | Near red 1 | 50 us | 100 us | ON - 0 | 600 |
|  |  |  |  | OFF- 50 US |  |
|  | Blue | 50 us | 500 us | ON - 150 us | 600 |
|  | Orange |  |  | OFF- 50 US |  |
|  | Green | 50 us | 50 us | ON - 0 | 600 |
|  | Ultraviolet |  |  | OFF- 50 US |  |
| Option 13 | Blue | 50 us | 50 us | ON - 150 us | 600 |
|  |  |  |  | OFF- 50 US |  |
|  | Green | 50 us | 50 us | ON - 0 | 600 |
|  |  |  |  | OFF- 50 US |  |
| Option 14 | Blue | 50 us | 50 us | ON - 150 us | 600 |
|  |  |  |  | OFF- 50 US |  |
| Option 15 | Near red | 50-100 us | 50-1500 us | ON - 0 OFF- 50 US | 600 to 1100 |
|  | Far Red | 50-100 us | 50-1500 us | ON - 100 us OFF- 150 us | 900 to 1100 |

EXAMPLES

The following examples are provided to illustrate further the various applications and are not intended to limit the invention beyond the limitations set forth in the appended claims.

Example 1-Regulation of Melatonin in Human

An adult male human (*Homo sapiens*), was exposed on Mar. 22, 2018 and Mar. 23, 2018 in Greeley, Colo. to supplemental pulsed lighting (Option 15 in Table 4 at 600 Ma for near red and 900 Ma for far red) approximately six hours during the night and eight hours during the day within a 24-hour period to assess melatonin levels under typical daily activities. Supplemental lighting was additive to normal environmental lighting, such as computers, television, etc.

Blood was collected from the Caucasian male human in his mid-40s. The first two samples were collected under ambient lighting conditions at 9 am and 5 pm. The subject was then exposed to supplemental pulsed lighting (Option 15 in Table 4) for 14 hours, including sleep, over the course of the next 24 hours and his blood was drawn at 9 am and 5 pm. A total of eight samples were drawn. The samples were taken from the antecubital area of the arm. The blood was collected using 25-gauge needles with 3cc syringes. The samples were immediately transferred to a lithium-heparin tube and inverted a total of ten times. The blood cells were centrifuged for 10 min at 3200 rpm using a Cole-Parmer centrifuge to isolate the plasma. The plasma samples were poured into 1.5 mL centrifuge tubes and placed into the freezer at $-17°$ C. The samples were prepared using the ab213978 melatonin ELISA kit from Abcam Labs. The samples were analyzed using a Varioskan LUX from Thermo Scientific.

All precipitates and solids were removed via centrifugation. Equal volumes (500 µL) of cold ethyl acetate and plasma sample were placed into an Eppendorf tube and gently vortexed. The layers were allowed to separate over ice. The sample was vortexed again and incubated over ice for two minutes. After, the samples were centrifuged at 1000 g for 10 min. The organic layer was carefully pipetted into a new tube. It was then dried over a stream of inert gas (Argon). Next, the pellet was suspended in 100-200 µL of 1× stabilizer. The sample was then kept on ice after the suspension and the assay was performed immediately.

The ELISA kit was purchased as a 96-well plate and ready to use upon arrival. The immunoassay was stored in a sealed pouch with desiccant in the refrigerator at $8°$ C. until the day of use.

All kit components were brought to room temperature. Plasma samples were used directly without any dilution. Next, 100 µL of sample was added to each well of a pre-coated well plate along with 100 µL of 1× stabilizer added to the blank wells. Then, 50 µL of 1X melatonin tracer and 50 µL of 1× melatonin antibody were added to each sample well except to the blank wells, respectively. The plate was sealed and incubated at room temperature (RT) on a shaker plate for 1 hour at about 500 rpm. After incubation, the samples were washed with the wash buffer a total of three times with 400 µL per well. After the last wash, the plate was emptied, and the contents were aspirated, and the plate was blot dried by tapping on a paper towel to remove any remaining wash buffer. Next, 200 µL of melatonin conjugate solution was added to each well expect to the blank wells. Again, the plate was sealed and was incubated at RT on a plate shaker for 30 minutes at about 500 rpm. The plate was washed again in the same manner as before and all the wash buffer was removed. At this point, 200 µL of TMB substrate solution was added to each well, and the plate was incubated for 30 minutes at RT on a shaker plate at the same rate as previously performed. Then, 50 µL of the stop solution was added to each well. Optical Density (OD) readings were recorded at a 450 nm wavelength by a plate reader.

Figure 20:
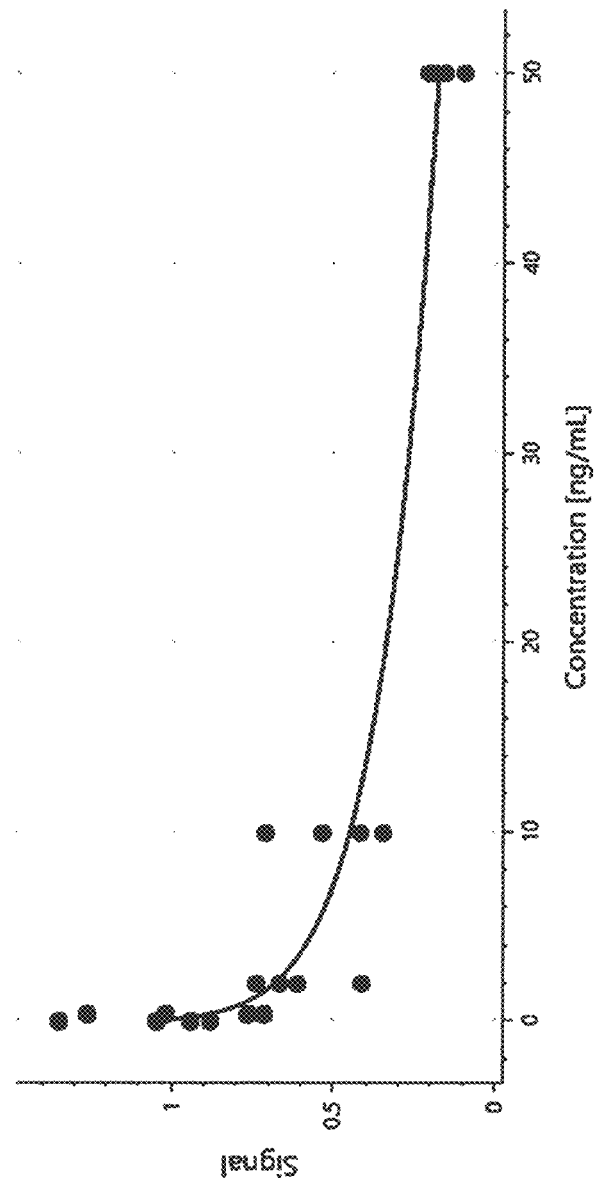
FIG. 20 is a Melatonin Elisa Kit Standard Curve showing the concentrations ranging from 0.04 ng/mL to 50 ng/mL. The reading of blank is not show on the plot because of the log-scale of X axis.

All data is presented as means using curve fitting programs (4-parameters) from the plate reader software (Skanit Software 5.0 for microplate readers). All the plots were created in excel. Known concentrations of melatonin antibody were pre-immobilized onto the plates. FIG. 20 shows the dilution curve for each pre-immobilized dilution (0, 50, 100, 250, 500, 1000 pg/mL) of melatonin antibody in the well plates.

Figure 21:
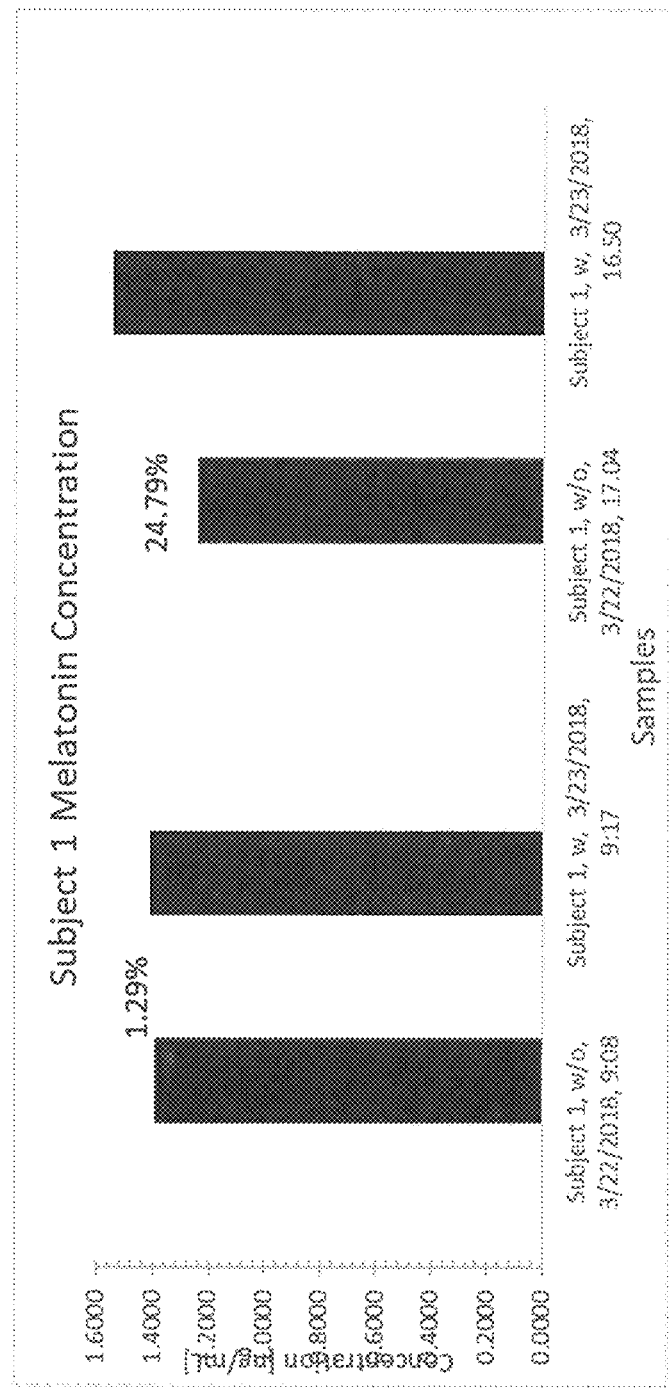
FIG. 21 is a Graph of melatonin concentrations in ng/mL. The control light is shown in the "Subject 1 w/o" and lights as described herein is shown in "Subject 1, w". All concentrations were calculated based on the standards shown in FIG. 20.

With known standards, the change in melatonin concentrations in ng/mL were obtained under lights (Option 15 in Table 4) as described herein and compared to a control light (FIG. 21). Blood was collected from a human subject over a two-day period. The first set of samples were collected approximately eight hours apart under standard light conditions. The second set of samples were collected under lights as described herein (Option 15 in Table 4) at the same time of day as the first set of samples, respectively. The samples were placed into 1.5 mL Eppendorf tubes and stored in the freezer at $-17°$ C. until the day of use. All the standards, blanks and samples were taken in replicate and averages were obtained.

Melatonin is a major factor in the circadian rhythm in mammals. Extensive research has shown that different light cycles effect melatonin production. This trial was conducted to determine the effect of lights as described herein on human melatonin levels.

The data in FIG. 21 shows that human melatonin levels increased by 24.79% after the first and second eight-hour timepoints. There was a greater increase in the melatonin level after a longer exposure to the lights (Option 15 in Table 4 at 600 Ma and 900 Ma) as described herein. The data would indicate that pulsing of lighting as described herein results in direct regulation of melatonin levels in humans.

Example 2—Regulation of Melatonin in Cattle

The 10-month-old black angus bull, raised in Yuma, Ariz. was placed in a 12×12 ft agricultural panel pen under normal lighting. After blood samples were collected for the first 3 timepoints (1400 hours, 2200 hours and 700 hours), the bull was housed in a tarped enclosure framed in by the agricultural panels and the only light source was a specific set of lights as described herein (Option 15 in Table 4 at 1100 Ma). Supplemental air into the tent was provided via an HVAC fan and was fed ad libitum grass hay and 5 pounds of sweet grain a day consistent with normal rations. Light intensity under lights as described herein (Option 15 in Table 4 at 1100 Ma) within the enclosure ranged from 52 to 1012 mW/m$^2$. If required, the bull was moved into a squeeze chute for blood collection and then returned to the enclosure.

Blood was collected from the bull at approximately eight (8) hour intervals. The first three samples were collected under ambient lighting conditions at 1400 hours, 2200 hours and 700 hours followed by a 74-hour exposure to a specific pulsed lighting recipe. Three additional samples were taken after the light exposure at approximately the same time of day as the initial blood collection (1400 hours, 2200 hours and 700 hours). The samples were taken from the coccygeal (tail) vein. The blood was collected using 23-gauge needles with 3cc syringes. The samples were immediately transferred to a lithium-heparin tube and inverted a total of ten times. The blood samples were centrifuged for 10 min at 3200 rpm using a Cole-Parmer centrifuge to isolate the plasma. The plasma samples were poured into 1.5 mL centrifuge tubes and placed into the freezer at $-17°$ C. The samples were prepared using the ab213978 melatonin ELISA kit from Abcam Labs. The samples were analyzed using a Varioskan LUX from Thermo Scientific.

All precipitates and solids were removed via centrifugation. Equal volumes (500 µL) of cold ethyl acetate and plasma sample were placed into an Eppendorf tube and gently vortexed. The layers were allowed to separate over ice. The sample was vortexed again and incubated over ice for two minutes. After, the samples were centrifuged at 1000 g for 10 min. The organic layer was carefully pipetted into a new tube. It was then dried over a stream of inert gas (Argon). Next, the pellet was suspended in 100-200 μL of 1× stabilizer. The sample was then kept on ice after the suspension and the assay was performed immediately.

The ELISA kit was purchased as a 96-well plate and ready to use upon arrival. The immunoassay was stored in a sealed pouch with desiccant in the refrigerator at 8° C. until the day of use.

All kit components were brought to room temperature. Plasma samples were used directly without any dilution. Next, 100 μL of sample was added to each well of a pre-coated well plate along with 100 μL of 1× stabilizer added to the blank wells. Then, 50 μL of 1X melatonin tracer and 50 μL of 1× melatonin antibody were added to each sample well except to the blank wells, respectively. The plate was sealed and incubated at room temperature (RT) on a shaker plate for 1 hour at about 500 rpm. After incubation, the samples were washed with the wash buffer a total of three times with 400 μL per well. After the last wash, the plate was emptied, and the contents were aspirated, and the plate was blot dried by tapping on a paper towel to remove any remaining wash buffer. Next, 200 μL of melatonin conjugate solution was added to each well except to the blank wells. Again, the plate was sealed and was incubated at room temperature on a plate shaker for 30 minutes at about 500 rpm. The plate was washed again in the same manner as before and all the wash buffer was removed. At this point, 200 μL of TMB substrate solution was added to each well, and the plate was incubated for 30 minutes at room temperature on a shaker plate at the same rate as previously performed. Then, 50 μL of the stop solution was added to each well. Optical Density (OD) readings were recorded at a 450 nm wavelength by a plate reader.

Figure 22:
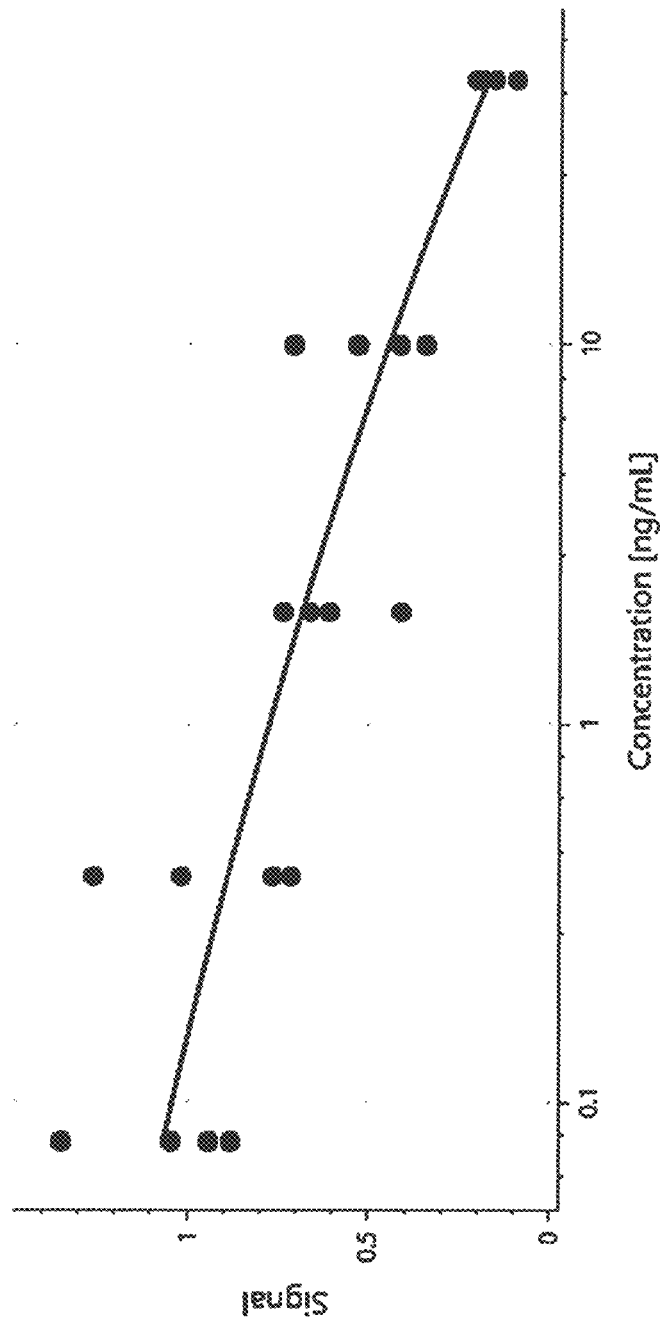
FIG. 22 is a Melatonin Elisa Kit Standard Curve showing the concentrations ranging from 0.04 ng/mL to 50 ng/mL. The reading of blank is not show on the plot because of the log-scale of X axis.

All data is presented as means using curve fitting programs (4-parameters) from the plate reader software (Skanit Software 5.0 for microplate readers). All the plots were created in excel. Known concentrations of melatonin antibody were pre-immobilized onto the plates. FIG. 22 shows the standard curve for each pre-immobilized dilution (50, 10, 2, 0.4, 0.08 ng/mL) of melatonin antibody in the well plates.

Figure 23:
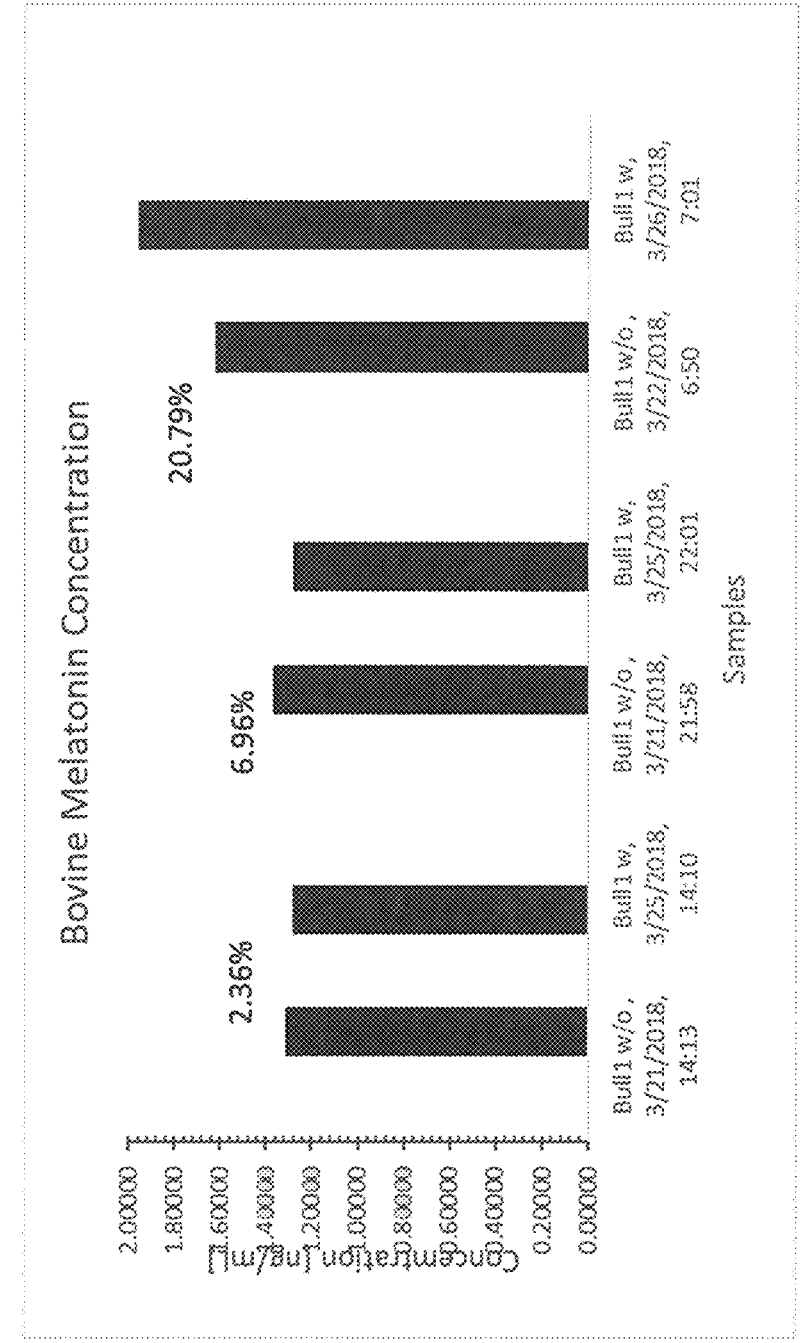
FIG. 23 is a Graph of bovine melatonin concentrations in ng/mL with and without lighting. The control light is shown in the "Bull 1 w/o" and lights as described herein is shown in "Bull 1, w". All concentrations shown are averages taken from replicate samples. All concentrations were calculated based on the standards shown in FIG. 22.

With known standards, the change in melatonin concentrations in ng/mL were obtained under lights as described herein and compared to a control light (shown in FIG. 23). Blood was collected from a bull over a five-day period. The first set of samples were collected every eight hours for a total of three times under the control light. The second set of samples were collected lights as described herein at the same time of day as the first set of samples, respectively. The samples were placed into 1.5 mL Eppendorf tubes and stored in the freezer at −17° C. until the day of use. All the standards, blanks and samples were taken in replicate and averages were obtained.

Melatonin is a major factor in the circadian rhythm in mammals. Extensive research has shown that different light cycles effect melatonin production. This trial was conducted to determine the effect of lights as described herein on bovine melatonin levels.

The data in FIG. 23 shows that the bovine melatonin levels increased by 20.79% with longer exposure to lights as described herein. After exposure to lights as described herein (Option 15 in Table 4 at 1100 Ma) for approximately 92 hours a significant increase of 20.79% was observed. The preliminary data would indicate that different lighting recipes can result in direct regulation over melatonin levels in bovine.

Example 3—Genetic Expression and Hormonal Excretion Found in Pigs

In another example, the light inputs of the systems and methods described herein affect genetic expression and hormonal excretion found in pigs. In both gilts and sows, seasonal infertility has many important economic impacts. Reduced farrowing rates are a result of increased numbers of gilts and sows returning to oestrus and insemination and a higher proportion of spontaneous abortions occurring from breedings completed during late summer and early autumn. This results in inefficient use of facilities and a decreased number of piglets being produced. Additionally, smaller litter sizes, increased time from weaning to oestrus and delayed puberty in gilts expected to mature between August and November in the norther hemisphere has been associated with long days. All of these factors contribute to the animal's non-productive days.

Example 4—Regulation of Circadian Rhythm in Mammals

In yet another example of light inputs and circadian rhythms affecting human genetic expression and hormonal excretion can be found in the spring forward effects from daylight savings time (DST). These affects are widespread and from modern research show effects ranging from a 10% increased myocardial infarction risk, 8% increased risk of cerebrovascular accidents, increase in suicides, and decreased in-vitro fertilization successes.

Example 5—Regulation of Circadian Rhythm in Mammals

In another example, dairy cattle, calves raised under long day photoperiods yield larger and leaner bodies at maturity with greater mammary parenchymal growth. Long day photoperiod exposed lactating cattle produced higher milk yield due to lower melatonin concentrations and higher prolactin concentration, whereas short day photoperiod during the dry period of multiparous cows enhances milk production in the following lactation. These items signify the importance of light exposure in dairy cattle for optimized production. Bovine somatotropins are a naturally occurring substance in cattle in order to maximize postpartum milk production. In the 1970's, rBST was created in using $E.\ coli$ in order to create an artificial growth hormone in dairy cattle. Unfortunately, studies have found that this artificial hormone causes many health effects in cattle including, 24% increase in cases of mastitis ($1.4 to $2.0 billion dollars per year economic impact), 40% reduced fertility, 55% increase in lameness. These side effects are not seen in naturally occurring BST which is created using the photo cues of existing light.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. A method of regulation of hormones in mammals, the method comprising:
   providing a system for pulsing photon signals toward a mammal comprising:
   at least one photon emitter;
   at least one photon emission modulation controller in communication with said at least one photon emitter;
   wherein said at least one photon emitter is configured to produce a photon signal to said mammal, wherein said wherein said photon signal comprises two or more independent components, wherein said two or more independent components comprise:
   a first independent component of a repetitive first modulated photon pulse group, wherein said first modulated photon pulse group has one or more first photon pulse ON durations with one or more first intensities, has one or more first photon pulse OFF durations, and a first wavelength color;
   wherein said one or more durations of said first photon pulse ON is between 0.01 microseconds and 10 milliseconds and wherein the one or more durations of the first photon OFF is between is between 0.1 microseconds and 24 hours; and
   a second independent component of a repetitive second modulated photon pulse group, wherein said second modulated photon pulse group has one or more second photon pulse ON durations with one or more second intensities, has one or more second photon pulse OFF durations, and a second wavelength color;
   wherein said one or more durations of said second photon pulse ON is between 0.01 microseconds and 10 milliseconds and wherein the one or more durations of the second photon OFF is between is between 0.1 microseconds and 24 hours;
   wherein the first independent component and the second independent component are produced within said signal simultaneously;
   wherein at least one aspect of the second modulated photon pulse group is different from the first modulated photon pulse group; and
   emitting said signal toward said mammal;
   wherein the combined effect of the signal regulates hormone levels in said mammal.

2. The method of claim 1, wherein the method further comprises establishing a baseline hormone level within a mammal before emitting said signal toward said mammal.

3. The method of claim 2, wherein said regulation is an increase in hormone production in said mammal.

4. The method of claim 3, wherein said hormone production is increased over said baseline level between 0.1% and 5000%.

5. The method of claim 2, wherein said regulation is a decrease in hormone production in said mammal.

6. The method of claim 5, wherein said hormone production is decreased under said baseline level between 0.1% and 5000%.

7. The method of claim 2, wherein said hormone baseline level is established using an analytical technique chosen from Enzyme immunoassay (ELISA), high-performance liquid chromatography (HPLC) and gas chromatography mass spectrometry.

8. The method of claim 1, wherein said hormone to be regulated is chosen from hypothalamic hormones and pituitary hormones.

9. The method of claim 8, wherein said hypothalamic hormones are chosen from corticotropin-releasing hormone, prolactin-releasing factors (serotonin, acetylcholine, opiates, & estrogens), somatostatin, and prolactin-inhibiting factors (dopamine).

10. The method of claim 8, wherein said pituitary hormones are chosen from Adrenocorticotropic hormone (ACTH), Melanocyte-stimulating hormone, Endorphins, Growth hormone, Luteinizing hormone (LH) and follicle-stimulating hormone (FSH), Thyroid-stimulating hormone (TSH), and Prolactin.

11. The method of claim 1, wherein said hormone is regulated in the brain, testis, liver, placenta, heart, lung, muscle, kidney, pancreas, or skin of said mammal.

12. The method of claim 1, wherein said hormone is melatonin.

13. The method of claim 1, wherein said first wavelength color of said first modulated photon pulse group has a wavelength between 0.1 nm and 1 cm; and
   wherein said second wavelength color of said second modulated photon pulse group photon pulse has a wavelength between 0.1 nm and 1 cm and is different from the first wavelength color of said first modulated pulse group.

14. The method of claim 1, wherein said first wavelength color of said first modulated photon pulse group has a near red wavelength; and
   wherein said second wavelength color of said second modulated photon pulse group photon pulse has a far-red wavelength.

15. The method of claim 1, wherein said first modulated pulse group has one or more photon pulse ON durations between 0.01 microseconds and 999 microseconds; and
   said second modulated pulse group has one or more photon pulse ON durations between 0.01 microseconds and 999 microseconds.

16. The method of claim 1, wherein said first modulated pulse group has one or more photon pulse ON durations between 999 microseconds and 10 milliseconds; and
   said second modulated pulse group has one or more photon pulse ON durations between 999 microseconds and 10 milliseconds.

17. The method of claim 1, further comprising:
   providing a master logic controller in communication with said at least one photon emission modulation controller, wherein said master logic controller sends commands to said at least one photon emission modulation controller controlling the one or more first photon pulse ON duration, the one or more first photon pulse OFF duration, the first photon pulse intensity, and the first photon pulse wavelength color and said one or more second photon pulse ON duration, the one or more second photon pulse delay OFF duration, the second photon pulse intensity, and the second photon pulse wavelength color from said at least one photon emitter.

18. The method of claim 17, further comprising:
   providing a power consumption sensor in communication with said master logic controller;
   monitoring the power usage of said at least one photon emitter;
   communicating said power consumption from said power consumption sensor to a host external to the master logic controller.

19. The method of claim 17, further comprising
   providing at least one sensor;

monitoring at least one condition associated with said mammal, wherein said at least one condition associated with said mammal is an environmental conditional associated with said mammal or a physiological condition associated with said mammal; and communicating data regarding said condition from said at least one sensor to said master logic controller.

20. The method of claim 19, further comprising:

adjusting said duration, intensity, wavelength band and duty cycle of said at least first modulated pulse group and said second first modulated pulse group based on the information from said power consumption sensor.

21. The method of claim 19, wherein said at least one sensor is selected from the group consisting of an air temperature sensor, humidity sensor, mammal body temperature sensor, mammal weight sensor, sound, movement sensor, infrared sensor, $O_2$ sensor, $CO_2$ sensor and CO and combinations thereof.

22. The method of claim 1, wherein all additional or supplemental light is obstructed from said mammal.

23. The method of claim 1, wherein said emission of said signal is a supplemental source of photons.

24. The method of claim 1, wherein said first modulated photon pulse group and said second modulated photon pulse group has a change in light quantum of at least 5%.

25. The method of claim 1, wherein the duty cycle of said first modulated photon pulse group and second modulated photon pulse group ranges between 0.1% to 93%.

26. The method of claim 1, wherein said method further regulates a desired response from said mammal, wherein said desired response is chosen from ovulation, hunger and mood.

27. The method of claim 26, wherein said desired response is said mammal is a response mediated by opsins in the hypothalamus of said mammal.

28. The method of claim 26, wherein said desired response is said mammal is a response mediated by the pineal gland of said mammal.

29. The method of claim 26, wherein said desired response in said mammal is a response mediated by the opsin in the brain, testis, liver, placenta, heart, lung, muscle, kidney, pancreas, or skin of said mammal.

30. The method of claim 1, wherein said regulation of hormones regulates said mammal's behavior, reproduction cycling, hair growth, calming or metabolism rates.

31. A method of regulation of hormones in mammals, the method comprising:

providing a system for pulsing photon signals toward a mammal comprising:

at least one photon emitter;

at least one photon emission modulation controller in communication with said at least one photon emitter;

wherein said at least one photon emitter is configured to produce a photon signal to said mammal, wherein said photon signal comprises two or more independent components, wherein said two or more independent components comprise:

a first independent component of a repetitive first modulated photon pulse group, wherein said first modulated photon pulse group has one or more first photon pulse ON durations with one or more first intensities, has one or more first photon pulse OFF durations, and a first wavelength color;

wherein said one or more durations of said first photon pulse ON durations are between 0.01 microseconds and 5000 milliseconds and wherein the one or more durations of the first photon OFF durations are between is between 0.1 microseconds and 24 hours;

and a second independent component of a repetitive second modulated photon pulse group, wherein said second modulated photon pulse group has one or more second photon pulse ON durations with one or more second intensities, has one or more second photon pulse OFF durations, and a second wavelength color;

wherein said one or more durations of said second photon pulse ON durations are between 0.01 microseconds and 5000 milliseconds and wherein the one or more durations of the second photon OFF durations are between is between 0.1 microseconds and 24 hours;

wherein the first independent component and the second independent component are produced within said signal simultaneously;

wherein the one or more first photon pulse ON durations of the first independent component are initiated at a different time and are offset from the one or more second photon pulse ON durations of the second independent component are produced within said signal simultaneously;

wherein second wavelength color of the second modulated photon pulse group is different from the second wavelength color of the first modulated photon pulse group;

and emitting said signal toward said mammal;

wherein the combined effect of the signal regulates hormone levels in said mammal.

32. The method of claim 31, wherein the method further comprises establishing a baseline hormone level within a mammal before emitting said signal toward said mammal.

33. The method of claim 32, wherein said regulation is an increase in hormone production in said mammal.

34. The method of claim 32, wherein said regulation is a decrease in hormone production in said mammal.

* * * * *